United States Patent
Becke et al.

(10) Patent No.: US 6,723,676 B2
(45) Date of Patent: Apr. 20, 2004

(54) 1,3-DISUBSTITUTED INDENE COMPLEXES

(75) Inventors: Sigurd Becke, Rösrath (DE); Thomas Weiss, Mannheim-Freudenheim (DE); Heinrich Lang, Chemnitz-Harthau (DE)

(73) Assignee: Bayer Aktiengesellschaft, Leverkusen (DE)

( * ) Notice: Subject to any disclaimer, the term of this patent is extended or adjusted under 35 U.S.C. 154(b) by 2 days.

(21) Appl. No.: 10/162,828

(22) Filed: Jun. 4, 2002

(65) Prior Publication Data

US 2003/0027954 A1 Feb. 6, 2003

(30) Foreign Application Priority Data

Jun. 8, 2001 (DE) .......................................... 101 27 926

(51) Int. Cl.[7] .............................. B01J 31/38; C08F 4/64; C08F 4/72
(52) U.S. Cl. ...................... 502/104; 502/117; 502/152; 502/155; 526/127; 526/160; 526/161; 526/348.6; 526/352; 556/11; 556/12; 556/20; 556/43; 556/53; 556/54
(58) Field of Search ................................ 502/104, 152, 502/155, 117; 556/11, 12, 20, 43, 53, 54; 526/160, 943, 161, 348.6, 351, 127

(56) References Cited

U.S. PATENT DOCUMENTS

| | | | |
|---|---|---|---|
| 5,026,798 A | 6/1991 | Canich | 526/127 |
| 5,068,325 A | 11/1991 | Grell et al. | 514/215 |
| 5,145,819 A | 9/1992 | Winter et al. | 502/117 |
| 5,276,208 A | 1/1994 | Winter et al. | 556/53 |
| 5,278,264 A | 1/1994 | Spaleck et al. | 526/127 |
| 5,329,033 A | 7/1994 | Spaleck et al. | 556/53 |
| 5,646,322 A | 7/1997 | van Beek et al. | 556/11 |
| 5,763,549 A | 6/1998 | Elder et al. | 526/153 |
| 5,807,939 A | 9/1998 | Elder et al. | 526/160 |
| 5,990,253 A | 11/1999 | van Beek et al. | 526/127 |
| 6,015,868 A | 1/2000 | Nickias et al. | 526/127 |
| RE37,208 E | 6/2001 | Winter et al. | 526/348 |
| 6,248,912 B1 * | 6/2001 | Lang et al. | 556/11 |
| RE37,384 E | 9/2001 | Winter et al. | 502/117 |
| 6,613,713 B2 * | 9/2003 | Becke et al. | 502/104 |

FOREIGN PATENT DOCUMENTS

| | | |
|---|---|---|
| EP | 0 277 003 | 8/1988 |
| EP | 0 277 004 | 8/1988 |
| EP | 0 520 732 | 12/1992 |
| EP | 0 941 997 | 9/1999 |
| EP | 0 942 011 | 9/1999 |
| WO | 95/00526 | 1/1995 |
| WO | 01/00693 | 1/2001 |
| WO | 01/30890 | 5/2001 |

OTHER PUBLICATIONS

Organometallics, (month unavailable) 1997, pp. 842–857, Cationic Metallocene Polymerization Catalysts Based on Tetrakis(pentafluorophenyl)borate and Its Derivatives. Probing the Limits of Anion "Noncoordination" by L. Jia, X. Yang, C. L. Stern and T. J. Marks.

(List continued on next page.)

*Primary Examiner*—Robert Harlan
(74) *Attorney, Agent, or Firm*—Joseph C. Gil; Jennifer R. Seng

(57) ABSTRACT

The present invention relates to organometallic compounds of transition metals with an indenyl ligand bonded in the 2-position and substituted in the 1,3-position, a process for their production, and their use as catalysts for the (co) polymerization of olefinic and/or diolefinic monomers.

18 Claims, 1 Drawing Sheet

OTHER PUBLICATIONS

Organometallics, (month unavailable) 1993, 12, pp. 5012–5015, "A Disulfone–Based Approach to ansa–Titanocenes: Synthesis of (Ethylenebis(2–indenyl)titanium Dichloride" by M. H. Nantz, S. R. Hitchcock, S. C. Sutton and M. D. Smith.

J. Am. Chem. Soc., 57, (month unavailable) 1935, pp. 2022–2026, "Some Bromine Derivatives of Indene and Indane" by H. D. Porter and C. M. Suter.

J. Org. Chem, (month unavailable) 1980, 45, pp. 4636–4641, "Generation of 2–Chloronaphthalene–1, 3–diyl" by W. E. Billups, J. D. Buynak and D. Butler.

Synthetic Communications, 20(9), (month unavailable) 1990, pp. 1387–1397, "Convenient Synthetic Preparation of Indanones" by I. Smonou and M. Orfanopoulos.

Monstsch Chem., 48, p. 341, "1, 2–Dihenylhydriden" by R. Weiss et al.

Database CA 'Online! Chemical Abstracts Service, Columbus, Ohio, US; Rakita, P. E. Et Al: "Organometallic rearrangements. II. Kinetics of the thermal isomerization of substituted silyl indenes" retrieved from STN Database accession No. 80:36535 XP002206864 RN 21220–3207 Zusammenfassung & J. Organometal. Chem. (1973), 61, 71–81.

Database CA 'Online! Chemical Abstracts Service, Columbus, Ohio, US; Yabunochi, Nobuhiro Et Al: "Organic hafnium compounds, olefin polymerization catalysts, and manufacture of olefin polymers" retrieved from STN Database accession No. 130:154092 XP002206865 RN 220211–83–6 RN 220211–96–1 Zusammenfassung & JP 11 005799 A (Idemitsu Petrochemical Co., Ltd., Japan) Jan. 12, 1999.

Gassman, Paul G. Et Al: "Synthesis of perfluoroalkylated indenes" J. Org. Chem. (1991), 56(17), 5143–6, XP001088481 Verbindungen 6, 7.

Kirihara, M. ; Kambayashi, T.; Momose, T.: "Allylic fluorides via cleave of tertiary cyclopropyl silyl ethers with diethylaminosulfur trifluoride" Chem. Commun., 1996, Seiten 1103–1104, XP002206859 Tabelle 1, Run 4.

Maury, Georges Et Al: "Reactivity of Alalylic systems of 2–benzylindene and 2–benzylideninden" Bull. Soc. Chim. Fr. (1974), (3, 4, Pt. 2), 623–6, XP001084409 Verbindungen 7, 8.

Database CA 'Online! Chemical Abstracts Service, Columbus, Ohio, US; Karlov, S. S. Et Al: "Organotin synthesis of 1–Hydro– and 1–(1–indenyl)germatranes" retrieved from STN Database accession No. 134:222812 XP002207160 Zusammenfassung & Russian Journal of General Chemistry (Translation of Zhurnal Obschchei Khimii) (2000), 70(6), 989–990.

Howa Jeong; Young Sam Park; Myong Sang Kim; Sang Tae Oh: Bulletin of the Korean Chemical Society, Bd. 22, Nr. 11, 2001, Seiten 1173–1174, XP002207159 siehe die Verbindungen 4.

Hitchcock, Shawn R. Et Al: "Synthesis of 6, 7 ansa–Titanocenes from 1, 2–Bis(2–indenyl)ethane and Structural Comparisons in the Catalytic Epoxidation of Unfunctionlized Alkenes" Organometallics (1995), 14(8), 3732–40, XP0009452344 Verbindungen 14, 15, 17.

Palandoken, Hasan Et Al: "Reductive dehydroxy coupling of 2–(hydroxymethyl)indenes to prepare ethano–bridged bis(2–indenyl) ansa–titanocenes" Journal of Organometallic Chemistry (1999), 579(1–2), 338–347, XP002206862 Verbindungen 8, 9.

Schaverien, Colin J. Et Al: "Ethylene Bis(2–indenyl) Zirconocenes: A New Class of Diastereomeric Metallocenes for the (Co)Polymerization of .alpha.—Olefins" Organometallics (2001), 20(16), 3436–3452 XP002206863 Verbindungen 1, 12, 15, 19, 25, 29.

J. Org. Chem. 25, (month unavailable) 1960, pp. 130–131, "An Attempt to Synthesize 3,5–Diphenylbenzocyclopentatriene" by C. F. Koelsch.

* cited by examiner

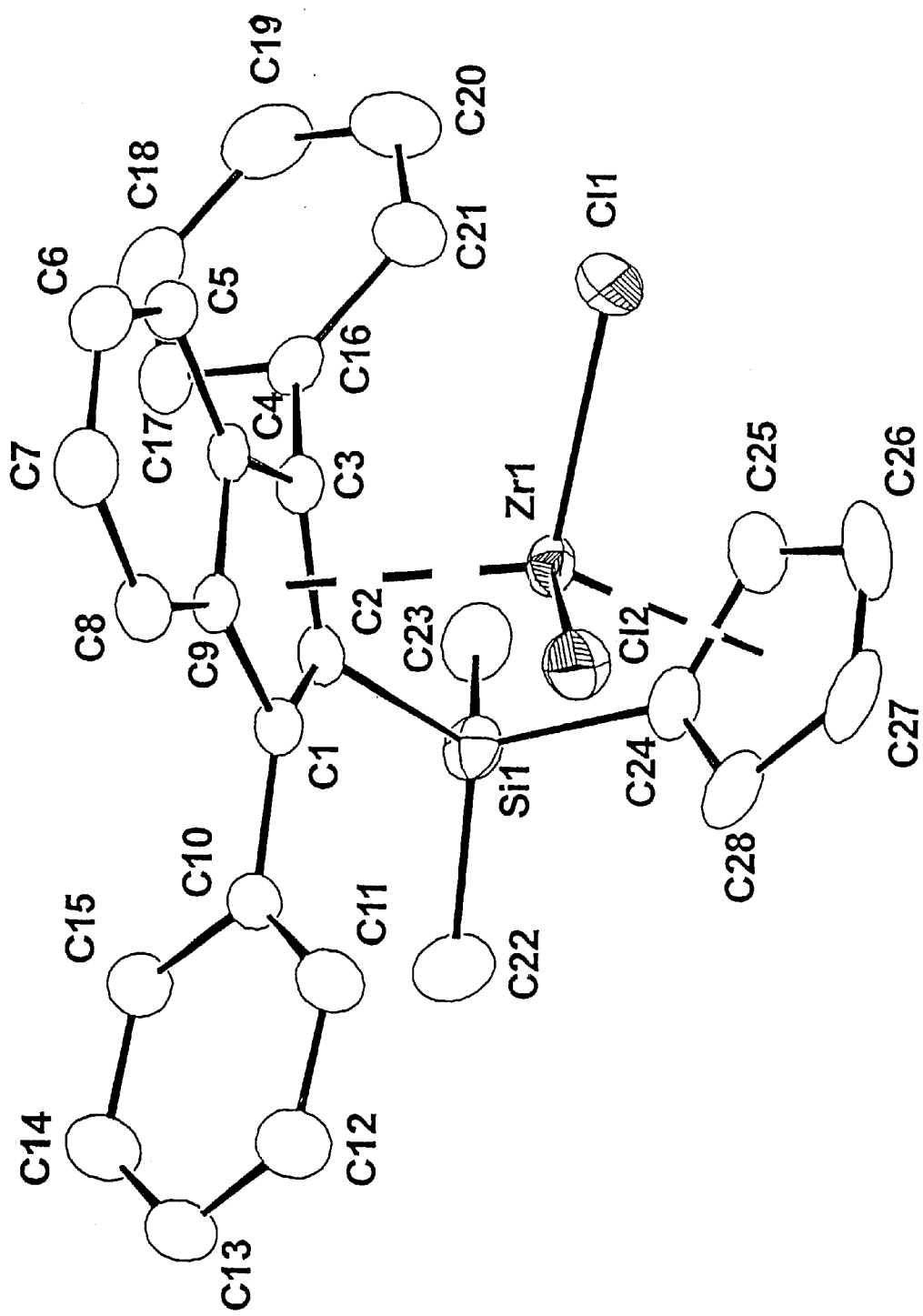

1,3-DISUBSTITUTED INDENE COMPLEXES

FIELD OF THE INVENTION

The present invention relates to organometallic compounds of transition metals with an indenyl ligand bound in the 2-position and substituted in the 1,3-position, a process for their production, and their use as catalysts for the (co)polymerization of olefinic and/or diolefinic monomers.

BACKGROUND OF THE INVENTION

Corresponding to the IUPAC nomenclature the positions of the ring atoms of indene are identified as follows in the present application:

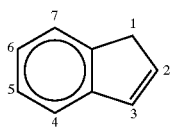

The production of substituted indenes [Spaleck, W.; Rohrmann, J.; Antberg, M.; EP-A1-0 530 647] is known in the relevant literature, and substituted indenes may be produced for example starting from 1-indanones [Smonou, I.; Ofranopopuolos, M. Synth. Commun. 1990, 20 (9), 1387].

The synthesis of 2-bromoindenes is based on known processes for their production [Billups, W.; J. Org. Chem. 1980, 23, 4638; Porter, H. D.; Suter, C. M. J. Am. Chem. Soc. 1935, 57, 2022; Koelsch, C. J. Org. Chem. 1960, 25, 130; Weiβ, R.; Luft, S.; Monatsh. Chem. 1927, 48, 341].

Stereorigid chiral metallocenes with bridged indenyl ligands are known as catalysts for the production of polyolefins. In this connection, it has been found that the nature and position of the substituents on the indenyl anion and the nature and position of the bridge have an influence on both the catalyst activity and also the polymer properties. Many of the indenyl metallocenes have a bridge in the 1-position (1-indenyl metallocenes).

The bis(1-indenyl)-metallocenes substituted in the 2- and/or 4-position with indenyl residues bridged in the 1-position are particularly important for the production of highly isotactic polypropylene with a high degree of crystallinity and a high melting point. (EP-A1-485 821, EP-A1-485 823, EP-A2-519237). Also important are the bis(1-indenyl)-metallocenes benzanellated in the 4,5-position (see Organometallics 1994, 13, 964–970).

It is also known to use organometallic compounds with only one indenyl anion as catalysts (constrained geometry complexes with 1-indenyl ligands, see U.S. Pat. No. 5,026,798, WO-97/15583-A1).

Organometallic compounds of transition metals that contain an indenyl ligand and a cyclopentadienyl ligand are known from WO-94/11406-A1, the indenyl ligand being substituted in the 2-position; this substituent may also be formed as a bridge to the second ligand. The examples of implementation illustrate multistage productions with extremely unsatisfactory yields that lead in the case of bridged compounds to 1-cyclopentadenyl-2-(2-indenyl)-ethane zirconium chloride, to bis-(2-indenyl)-methane zirconium dichloride, or to dimethyl-bis-(2-indenyl)-silane zirconium dichloride, which still contains impurities. A multistage synthesis pathway to ethylene-bis-(2-indenyl) titanium dichloride is described in Organometallics 1993, 12, 5012–5015. On account of the multistage synthesis and the numerous purification operations the achievable yield is very low. On account of the synthesis pathway the structural multiplicity is restricted to ethylene-bridged ligands.

Ethylene-bridged bis(2-indenyl) zirconocenes are disclosed in EP-A2-941 997. These zirconocenes are used for the production of special polyolefins with low molecular weights.

Silyl-bridged 2-indenyl metallocenes and a process for the production of organometallic compounds with an indenyl ligand bonded in the 2-position are described in EP-A1-0 940 408.

Moreover, a process for the production of amorphous polypropylenes using a catalyst system based on monocyclopentadienyl transition metal complexes is described in U.S. Pat. No. 5,504,169. The cyclopentadienyl ring bonded to the transition metal complex is substituted symmetrically with no, two or four substituents.

Transition metal complexes with 1,3-disubstituted indenyl ligands bridged in the 2-position are not known.

It has now been shown that such organometallic catalysts whose bridging attaches at least one 1,3-disubstituted indenyl anion to the 2-position have special properties as polymerization catalysts; they produce in fact predominantly atactic polymers with high molecular weights in the (co) polymerization of α-olefins. It was, therefore, desirable to find a production process for such catalysts bridged in the 2-position by at least one 1,3-disubstituted indenyl anion.

A further object of the invention was to provide a catalyst that is suitable for the synthesis of high molecular weight EPDM.

SUMMARY OF THE INVENTION

The present invention relates to a process for the production of organometallic compounds of transition metals with 2-indenyl ligands substituted in the 1,3-position that correspond to the general formula (I),

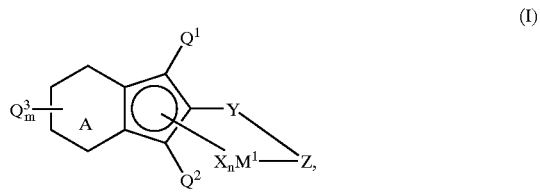

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge from the group of —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—, |O$R^5$— or |S$R^5$—, wherein the vertical line to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —O$R^1$, —S$R^1$ or —N($R^1R^2$), characterized in that a halogenated indene substituted in the 1,3-position of the formula (II)

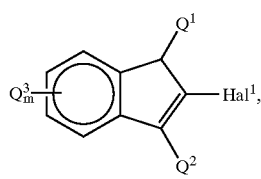

(II)

in which $Hal^1$ denotes Cl, Br or I and $Q^1$, $Q^2$ and $Q^3$ and m have the above meanings, is reacted with an elementary metal selected from Groups I, II or XII of the Periodic System according to IUPAC 1985 or a corresponding metal compound in an amount in the range from 1 to 100 moles of elementary metal/metal compound per mole of (II) and with a dihalide of the bridge Y of the formula

(III), in which $Hal^2$ and $Hal^3$ independently of one another denote Cl, Br or I and Y has the above range of meanings, in an amount of 1 to 20 moles of (III) per mole of (II), wherein in the case where Y has the meaning —Si($R^1R^2$)—, —Ge($R^1R^2$)— or —Si($R^1R^2$)—Si($R^3R^4$)—, the reaction of (II) with (i) elementary metal/metal compound, and of (ii) with (III) may also take place simultaneously, and the reaction product of the formula

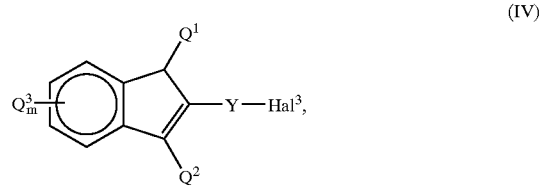

(IV)

wherein $Q^1$, $Q^2$, $Q^3$, Y and $Hal^3$ have the above meanings, is reacted, optionally after it has been separated, with a Z derivative of the formula

(Va)

or

(Vb), in which $M^2$ denotes Li, Na, K or —Mg$Hal^4$, wherein $Hal^4$ has the range of meanings of $Hal^2$, p represents the number 1 or 2, $R^9$ denotes hydrogen, —Si($R^1R^2R^3$) or Sn($R^1R^2R^3$), and Z, $R^1$, $R^2$ and $R^3$ have the above meanings, with the release of a compound of the formula

(VIa)

or

(VIb), in which $M^2$, $R^9$ and $Hal^3$ have the above meanings, optionally in the presence of an auxiliary base to form the 2-indenyl compound of the formula

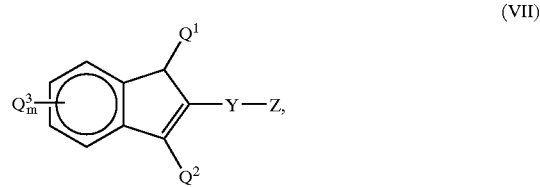

(VII)

in which $Q^1$, $Q^2$, $Q^3$, Y, Z and m have the above meanings and which may be present as a dianion, and in which Z may furthermore carry $M^2$, $R^9$ or an electron pair, and is then reacted further with a transition metal compound of the formula

(VIII), in which $M^1$ and X have the above meanings and q is a number from 2 to 6 that is determined by the oxidation state of $M^1$.

BRIEF DESCRIPTION OF THE DRAWING

FIG. 1 shows an X-ray structure analysis of 2-(cyclopentadienyl-methylsilyl)-1,3-diphenylindene zirconocene dichloride.

DETAILED DESCRIPTION OF THE INVENTION

The process is advantageously carried out at temperatures in the range from −100° to 120° C.

As metals of Groups I, II or XII, there may, in particular, be mentioned lithium, potassium, sodium, magnesium, calcium, zinc, cadmium and mercury. Metals of Groups II and XII are preferred. It may also be advantageous to use the metals mixed with one another.

As corresponding metal compounds there may be mentioned butyllithium, butadiene magnesium, anthracene magnesium, as well as the corresponding compounds of the other mentioned metals.

It may be advantageous to separate the unreacted metals/metal compounds before the addition of (III).

As a rule the corresponding metal halides, i.e. metal $Hal^1Hal^2$, are formed in the reaction with (III).

Furthermore, as a rule the corresponding compounds of the formulae $$M^2Hal^3 \quad \text{(VIa)}$$

or $$R^9Hal \quad \text{(VIb)},$$

in which $M^2$, $R^9$ and $Hal^3$ have the known meanings, are formed on the addition of (Va) or (Vb).

Furthermore, the invention relates to the organometallic compounds of transition metals with 2-indenyl substituted in the 1,3-position as ligand that can be produced by the aforementioned process and that correspond to the general formula (I)

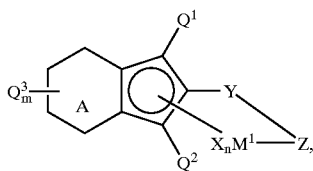

(I)

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphos-phoryl or phenyl-$C_1$–$C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge from the group comprising —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—Si($R^3R^4$)—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—, |O$R^5$— or |S$R^5$—, wherein the vertical line to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —O$R^1$, —S$R^1$ or —N($R^1R^2$).

Moreover, the invention relates to the use of the compounds according to formula (I) as catalysts on a catalyst support (e.g. $Al_2O_3$, $SiO_2$ and other inert supports) as well as without a support, for the polymerization of monomers from the group comprising $C_2$–$C_6$-α-olefins, $C_4$–$C_6$-diolefins and cyclo(di)olefins or for the copolymerization of several of the aforementioned monomers, in particular for the production of amorphous, predominantly atactic polymers.

The invention preferably relates to the aforedescribed process and the compounds of the formula (I) that can be produced thereby, wherein Y has the meaning —Si($R^1R^2$)—, —Ge($R^1R^2$)— or —Si($R^1R^2$)—Si($R^3R^4$)—, particularly preferably —Si($R^1R^2$)—, and the reaction of (II) with (i) Mg or Zn, and of (ii) with (III) to form the reaction product (IV) takes place simultaneously.

The present invention also relates to intermediate products of the formula

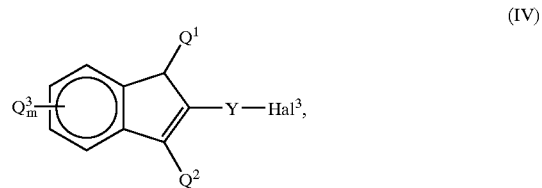

(IV)

wherein $Q^1$, $Q^2$, $Q^3$, Y and $Hal^3$ have the aforementioned meanings.

Cyclic π-systems within the scope of the meaning of Z are, for example, substituted or unsubstituted cyclopentadiene, substituted or unsubstituted 1-indene, substituted or unsubstituted 2-indene or substituted or unsubstituted fluorene, which are bonded covalently to the bridge Y and are bonded ionically, covalently or co-ordinatively to $M^1$.

The invention relates in a preferred way to the process according to the present invention and to organometallic compounds of transition metals according to the present invention of the formula (I), in which however the second Z' replaces Z, Z' denoting substituted or unsubstituted cyclopentadiene, substituted or unsubstituted 1-indene, substituted or unsubstituted 2-indene, substituted or unsubstituted fluorene, —N($R^5$)—, —P($R^6$)—, |N($R^5R^7$)—, |P($R^6R^8$)—, —O—, —S—, |$OR^5$— or |$SR^5$—, wherein $R^5$ to $R^8$ and the vertical lines have the aforementioned meanings.

Also preferred are those compounds of the formula in which Z" denotes —N($R^5$)— or |N($R^5R^7$)—, in particular in conjunction with Y=—Si($R^1R^2$)— and $M^1$=Ti or Zr.

Straight-chain or branched $C_1$–$C_{10}$-alkyl denotes, for example, methyl, ethyl, propyl, isopropyl, butyl, isobutyl, tert.-butyl, the isomeric pentyls, hexyls, octyls or decyls. $C_1$–$C_4$-alkyl is preferred, methyl and ethyl being more preferred.

$C_5$–$C_8$-cycloalkyl is, for example, cyclopentyl, methylcyclopentyl, dimethylcyclopentyl, cyclohexyl, methylcyclohexyl, dimethylcyclohexyl, cycloheptyl, cyclooctyl, preferably cyclopentyl and cyclohexyl, and their methyl and dimethyl derivatives.

$C_6$–$C_{14}$-aryl is for example phenyl, naphthyl, biphenyl, anthryl, phenanthryl, preferably phenyl.

$C_7$–$C_{10}$-aralkyl is, for example, benzyl, α-phenylethyl or β-phenylethyl, phenylpropyl or phenylbutyl.

$C_1$–$C_4$-alkoxy and $C_1$–$C_4$-alkylthio are, for example, methoxy, methylthio, ethoxy, ethylthio, propoxy, propylthio, isopropoxy, isopropylthio, butoxy, butylthio, isobutoxy and isobutylthio.

Aryl and the aromatic fractions of aralkyl may be singly or doubly, identically or differently substituted by fluorine, chlorine, bromine, methyl, ethyl, methoxy or ethoxy.

$Q^3$ is, for example, H or $CH_3$, in the 4-, 5-, 6-, 7-positions.

Halogen within the scope of $R^1$ to $R^8$ is, for example, fluorine, chlorine, bromine or various of these, preferably chlorine.

$M^1$ is, for example, Ti, Zr, Hf, V, Nb, Ta, Cr, W, Mo, preferably Ti, Zr, Hf, V, Nb, more preferably Ti, Zr, Hf, and most preferably Ti and Zr. $M^1$ may be used in the highest possible oxidation state as well as in a lower oxidation state different therefrom and may thus appear as such in the organometallic compounds. In many cases, it is advantageous to employ $M^1$ first of all in a low oxidation state and then to oxidise it to a higher state with a mild oxidizing agent, for example $PbCl_2$.

X is a singly or multiply charged anion from the group comprising fluoride, chloride, bromide, $C_1$–$C_4$-carboxylate, amide, $C_1$–$C_4$-alkyl, phenyl, benzyl, neopentyl and substituted or unsubstituted butadienyl, preferably chloride or fluoride; also, various of the aforementioned anions may be present.

$Hal^1$, $Hal^2$ and $Hal^3$ within the scope of (II) and (III) are independently of one another Cl, Br or I; preferably $Hal^1$ is Br and $Hal^2$ and $Hal^3$ are Cl or Br.

The temperature of the reaction of (II) with Mg or Zn is in the range from −20° C. to +120° C., preferably 0° C. to +100° C., more preferably +25° C. to +80° C.

The amount of Mg or Zn is 1 to 100 moles per mole of (II). In principle, the reaction may also be carried out with amounts outside the aforementioned range. Below 1 mole of Mg or Zn per mole of (II), the reaction of (II) is incomplete, while above 100 moles there is no further advantage to be expected as regards completeness and speed of the reaction. Preferably 1 to 10 moles of Mg or Zn and more preferably 1 to 5 moles of Mg or Zn are used per mole of (II). Of the metals Mg and Zn, it is preferred to use Mg for the reaction.

The temperature for the further reaction with (III) is also in the range from −20° C. to +120° C., preferably 0° C. to +100° C., more preferably +25° C. to +80° C.

The amount of (III) is 1 to 20 moles per mole of (II). The comments made above regarding the amount of Mg or Zn apply to amounts outside this range. Preferably, 1 to 10 moles of (III) and more preferably, 1 to 2 moles of (III) are used per mole of (II).

Unreacted Mg or Zn and (III) are separated from the reaction batch in a manner known per se to those skilled in the art and may be re-used.

The process according to the present invention may be carried out in the presence of a polar, aprotic solvent. Suitable solvents are, for example, methylene chloride, chloroform, dimethylformamide, N-methylpyrrolidone and ethers. Of these solvents, ethers are preferred, for example, diethyl ether, diisopropyl ether, dioxane, tetrahydrofuran and other ethers known to the person skilled in the art. The amount of solvent is chosen so that (II) and the organo-Mg or organo-Zn compound formed, therefrom, are present in dissolved form and the unreacted Mg or Zn may be separated for example by filtration or decanting or by similar separation operations. The amount of solvent is, for example, 50 to 1000% of the amount of (II).

Y is preferably —C($R^1R^2$)—, —Si($R^1R^2$)—, more preferably —Si($R^1R^2$)—.

In the case where Y denotes —Si($R^1R^2$)—, —Ge($R^1R^2$)— or —Si($R^1R^2$)—Si($R^3R^4$)—, the simultaneous reaction of (II) with (i) Mg or Zn, and of (ii) with (III) provides an elegant possible way of saving a reaction stage.

In the case, where the reaction of (IV) with (Va) or (Vb) to form (VII) is carried out in the presence of an auxiliary base, suitable examples of the latter include: open-chain or cyclic tertiary aliphatic amines with a total of 3 to 30 C atoms, such as trimethylamine, triethylamine, tripropylamine, triisopropylamine, tributylamine, triisobutylamine, trihexylamine, trioctylamine, tridecylamine, N-methylpiperidine, N,N'-dimethylpiperazine, diazabicyclononane (DBN), diazabicycloundecane (DBU), as well as amines with variously long C chains, such as N,N-dimethylbutylamine, N,N-dimethyloctylamine, N,N-dimethylstearylamine and the like, and aromatic amines such as pyridine, methylpyridines, quinoline, N,N-dimethylaniline and the like.

The reaction mixture containing the organometallic compound (I) is worked up by operations known to the person skilled in the art, such as filtration, distilling off volatile fractions of the mixture, and crystallization.

The present invention additionally relates to the use of compounds according to formula (I) as catalysts on a catalyst support (e.g. $Al_2O_3$, $SiO_2$ and other inert supports) as well as without a support, for the polymerization of monomers from the group comprising $C_2$–$C_6$-α-olefins, $C_4$–$C_{20}$-diolefins and cyclo(di)olefins, or for the copolymerization of several of the aforementioned monomers, in particular for the production of amorphous, predominantly atactic polymers.

The organometallic compounds of the formula (I) may be used as catalysts for the (co)polymerization of $C_2$–$C_{12}$-α-olefins, $C_4$–$C_{20}$-diolefins, cyclo(di)olefins or mixtures of several of the latter. Monomers of the aforementioned groups are for example: ethylene, propylene, 1-butylene, 1-pentene, 1-hexene, 1-octene and their branched isomers, isobutylene, 1,3-butadiene, 1,3-pentadiene or 1,4-pentadiene, 1,3-hexadiene, 1,4-hexadiene or 1,5-hexadiene, 1,5-heptadiene, isoprene, chloroprene, norbornene, 5-ethylidene-2-norbornene, 5-vinyl-2-norbornene, 4-vinyl-1-cyclo-hexene, dicylcopentadiene, 7-methyl-1,6-octadiene and 5,7-dimethyl-1,6-octadiene.

Compounds of the formula (I) in which Y=—Si($R^1R^2$)—, $M^1$=Ti or Zr and Z=—N($R^5$)— are suitable, in particular, for the production of atactic polypropylene.

The compounds of the formula (I) are used for the (co)polymerization, frequently in combination with co-catalysts.

Suitable co-catalysts are co-catalysts known in the field of metallocene chemistry, such as polymeric or oligomeric alumoxanes, Lewis acids as well as aluminates and borates. In this connection, reference is made, in particular, to Macromol. Symp. Vol. 97, July 1995, pp. 1–246 (for alumoxanes), as well as EP-A1-277 003, EP-A1-277 004, Organometallics 1997, 16, 842–857 (for borates) and EP-A2-573 403 (for aluminates).

Particularly suitable as co-catalysts are methyl alumoxane, methyl alumoxane modified by triisobutylaluminum (TIBA), as well as diisobutyl alumoxane, trialkylaluminum compounds such as trimethylaluminum, triethylaluminum, triisobutylaluminum, triisooctylaluminum, furthermore dialkylaluminum compounds such as diisobutylaluminum hydride, diethylaluminum chloride, substituted triarylboron compounds such as tris(pentafluorophenyl)borane, as well as ionic compounds that contain tetrakis(pentafluorophenyl)borate as anion, such as triphenylmethyl-tetrakis(pentafluorophenyl)borate, trimethylammoniumtetrakis(pentafluorophenyl)borate, N,N-dimethylaniliniumtetrakis(pentafluoro-phenyl)-borate, substituted triarylaluminum compounds such as tris (pentafluorophenyl)-aluminum, as well as ionic compounds that contain tetrakis(pentafluorophenyl)-aluminate as anion, such as triphenylmethyl-tetrakis(pentafluorophenyl) aluminate and N,N-dimethylaniliniumtetrakis (pentafluorophenyl)aluminate.

Obviously, it is possible to use the co-catalysts mixed with one another. The most favorable mixing ratios in each case should be determined by appropriate preliminary experiments.

Such (co)polymerizations are carried out in the gaseous, liquid or slurry phase. The temperature range in this connection is from −20° C. to +200° C., preferably 0° C. to 160° C., more preferably +20° C. to +80° C.; the pressure range extends from 1 to 50 bar, preferably 3 to 30 bar. Co-used solvents include for example saturated aliphatic or (halogen) aromatic compounds such as pentane, hexane, heptane, cyclohexane, petroleum ether, petroleum, hydrogenated ligroins (benzines), benzene, toluene, xylene, ethylbenzene, chlorobenzene and the like. These reaction conditions for the (co)polymerization are in principle known to the person skilled in the art.

Important polymers that may be produced with the organometallic compounds according to the present invention as catalysts are those of ethylene and copolymers thereof. Suitable comonomers are $C_2$–$C_{12}$-alkenes such as ethylene, 1-butene, 1-pentene, 1-hexene, 1-octene and arylalkenes such as, for example, styrene. Other suitable comonomers are non-conjugated dienes such as 1,4-hexadiene, 1,5-heptadiene, 4-vinyl-1-cyclohexene, 7-methyl-1,6-octadiene and 5,7-dimethyl-1,6-octadiene, 5-ethylidene-2-norbornene, 5-vinyl-2-norbornene and dicyclopentadiene. It is also possible to use mixtures of the aforementioned comonomers.

The ethylene (co)polymers that can be produced in this way have molecular weights of $M_n$>100,000 g/mole and molecular weight distributions of $M_w/M_n$<4. The ethylene (co)polymers have intrinsic viscosities greater than 1 dl/g, preferably greater than 2 dl/g. The crystallinities are less than 15%, the percentage crystallinity=(enthalpy of fusion/ 209 J/g)×100 and the enthalpy of fusion in J/g being determined by the DSC method. More preferred are ethylene (co)polymers with enthalpies of fusion of less than 5 J/g (DSC method). The ethylene (co)polymers are readily soluble in conventional solvents such as hexane, heptane, diethyl ether or toluene.

In particular, rubbers based on ethylene and one or more of the aforementioned comonomers can also be produced in the aforedescribed manner. A more preferred embodiment is the copolymerization of ethylene and propylene, in which amorphous ethylene (co)polymers with an ethylene fraction in the polymer in the range from 30 to 70 wt. %, preferably 40 to 65 wt. %, are obtained.

EPDM rubbers based on ethylene, propylene and a diene, preferably 5-ethylidene-2-norbornene, can also be produced in the aforedescribed way. The EPDM rubbers are characterized in that they have high molecular weights and low crystalline fractions.

High molecular weight atactic polymers, e.g. atactic polypropylene, can be produced particularly well with the organometallic compounds according to the present invention.

For example, the (co)polymerization of ethylene with or without the aforementioned comonomers may be carried out as follows: a steel autoclave is cleaned in the conventional manner and is then filled with a solvent and a scavenger, e.g. triisobutylaluminum. Possible impurities and catalyst poisons, for example, water or other oxygen-containing compounds, are rendered harmless by the scavenger. A compound of the formula (I) is next added as catalyst precursor. The reactor is then charged with monomers up to a certain pressure, thermostatically controlled at a selected temperature, and the polymerization is started by adding one or more of the previously mentioned co-catalysts. The polymerization may be carried out in a continuous or batchwise process.

EXAMPLES

The invention is described in more detail with the aid of the following examples.

General information: production and handling of organometallic compounds is carried out under the exclusion of air and moisture and under an argon protective atmosphere (Schlenk technique). All the necessary solvents were dehydrated before use by boiling for several hours over a suitable drying agent followed by distillation under argon. The compounds were characterised by $^1$H-NMR, $^{13}$C-NMR and infrared spectroscopy.

Polymer Characterization

The intrinsic viscosity was determined in an Ubbelohde capillary viscosimeter at 140° C. in o-dichlorobenzene as solvent (multipoint measurement). The DSC measurements were performed in a Perkin-Elmer instrument (differential scanning calorimeter DSC-2) according to the following procedure: two heating régimes −90° C., up to +180° C., heating rate 20 K/min, rapid cooling at 320 K/min to −90° C., rinsing with nitrogen, and weighing out 12.3 mg of sample in standard capsules. The NMR measurements to determine the microstructure were carried out in tetrachloroethane using a Bruker DRX-400 instrument. The determination of the Mooney viscosity was carried out according to ASTM 1646/DIN 53 523 at a temperature of 125° C. The IR spectroscopy determination of the polymer composition was carried out according to ASTM D 3900.

| Abbreviations: | |
|---|---|
| TIBA | triisobutylaluminum |
| I.V. | intrinsic viscosity |

Example 1
Production of 3-methylindan-1-one 3-phenylbutyric acid (26.1 g, 0.159 mole) is reacted at 25° C. in one portion with thionyl chloride (28.4 g, 17.3 ml, 0.24 mole). The reaction mixture is heated for 4 hours under reflux and stirred for 15 hours at 25° C. The excess thionyl chloride is distilled off from the reaction mixture (b.p.: 79° C.). The orange-brown oil that is obtained is dissolved in 100 ml of benzene and cooled to 0° C. $AlCl_3$ is then added in portions (21.0 g, 0.159 mole). The reaction mixture is stirred for 30 minutes at 25° C. and then heated for 1.5 hours under reflux. After the end of the reaction, the mixture is poured onto 400 ml of iced water and acidified with concentrated hydrochloric acid to pH=1. The organic phase is now separated in a separating funnel, the aqueous phase is extracted once with 30 ml of benzene, and the combined organic phases are dried over $Na_2SO_4$. The volatile constituents are removed in a rotary evaporator (40° C., 240 mbar) and the residue is distilled under an oil pump vacuum at 78° C. A yellow liquid is obtained.

Yield: 21.0 g (0.144 mole, 90% of theory referred to 3-phenylbutyric acid). $^1$H-NMR in $CDCl_3$, 300.0 MHz, [δ]: 1.29 (d, 3 H, $^2J_{HH}$=6.0 Hz, $CH_3$), 2.20 (dd, 1 H, $^1J_{HH}$=21.0 Hz, $^2J_{HH}$=0.9 Hz, $CH_2$), 2.20 (dd, 1 H, $^1J_{HH}$=21.0 Hz, $^2J_{HH,cis}$=0.9 Hz, $CH_2$), 2.79 (dd, 1 H, $^1J_{HH}$=21.0 Hz, $^2J_{HH,trans}$=9.0 Hz, $CH_2$), 3.32 (ddd, 1 H, $^2J_{HH,\ trans}$=9.0 Hz, $^2J_{HH}$=6.0 Hz, $^2J_{HH,\ cis}$=0.9 Hz, C$\underline{H}$—$CH_3$), 7.25 (pt, 1 H, $^2J_{HH}$=9.0 Hz, CH), 7.40 (pd, $^2J_{HH}$=3.0 Hz, CH), 7.49 (pt, 1 H, $^2J_{HH}$=6.0 Hz, CH), 7.61 (pd, 1 H, $^2J_{HH}$=4.5 Hz, CH).

$^{13}C\{^1H\}$-NMR in $CDCl_3$, 75.5 MHz, [δ]: 21.0 ($CH_3$), 32.4 ($CH_2$), 44.9 ($\underline{C}H$—$CH_3$), 123.0 (CH), 125.0 (CH), 127.0 (CH), 134.4 (CH), 136.0 ($C_{ipso}$), 159.6 ($C_{ipso}$), 205.9 (C, CO).

IR (NaCl) in $cm^{-1}$: 3070 (s), 3050 (s), 2961 (s, broad), 1713 (s) [$v_{c=o}$], 1605 (s), 1460 (s), 1405 (m), 1375 (w), 1325 (s, broad), 1280 (s, broad), 1241 (m), 1213 (m), 1177 (m), 1151 (m), 1096 (s), 1042 (m), 1012 (m), 760 (s, broad).

Example 2
Production of 3-phenylindan-1-one

Thionyl chloride (19.6 g, 12 ml, 0.17 mole) is added to 3,3-diphenylpropionic acid (26.0 g, 0.11 mole), heated for 4 hours under reflux, and stirred for 15 hours at 25° C. The excess thionyl chloride is now distilled off (b.p.: 79° C.). An orange-brown oil remains, which is dissolved in 100 ml of benzene. The solution obtained is cooled to 0° C. and $AlCl_3$ (16.0 g, 0.11 mole) is added thereto in portions. The reaction mixture is stirred for 30 minutes at 25° C. and then heated for 1.5 hours under reflux. After the end of the reaction, the mixture is poured onto 400 ml of iced water and the pH is adjusted to 1 with the concentrated hydrochloric acid. The organic phase is separated in a separating funnel, the aqueous phase is extracted once with 30 ml of benzene, and the combined organic phases are dried over $Na_2SO_4$. The volatile constituents are removed on a rotary evaporator and the residue is distilled under an oil pump vacuum at 155° C. An orange solid is obtained.

Yield: 15.8 g (0.076 mole, 69% of theory referred to 3,3-diphenylpropionic acid).

M.p.: 75° C.

$^1$H-NMR in $CDCl_3$, 300.0 MHz, [δ]: 2.70 (d, 1 H, $^1J_{HH}$=15.0 Hz, $^2J_{HH,cis}$=3.0 Hz, $CH_2$), 3.24 (dd, 1 H, $^1J_{HH}$=15.0 Hz, $^2J_{HH,trans}$=9.0 Hz, $CH_2$), 4.58 (dd, 1 H, $^2J_{HH,\ trans}$=9.0 Hz, $^2J_{HH,\ cis}$=3.0 Hz, $CH_2$), 7.12 (pd, 1 H, $^2J_{HH}$=6.0 Hz, $C_9H_4$), 7.2–7.4 (m, 5 H, $C_6H_5$), 7.42 (pt, 1 H, $^2J_{HH}$=7.5 Hz, CH, $C_9H_4$), 7.57 (pt, 1 H, $^2J_{HH}$=6.6 Hz, CH, $C_9H_4$), 7.82 (pd, 1 H, $^2J_{HH}$=7.5 Hz, CH, $C_9H_4$).

$^{13}C\{^1H\}$-NMR in $CDCl_3$, 75.5 MHz, [δ]: 44.3 ($\underline{C}H$—$C_6H_5$), 46.7 ($CH_2$), 123.3 (CH), 126.8 (CH), 126.9 (CH), 127.5 (CH), 127.5 (CH), 127.8 (CH), 128.5 (CH), 128.8 (CH), 135.0 (CH), 136.6 ($C_{ipso}$), 143.5 ($C_{ipso}$), 157.9 ($C_{ipso}$), 206.0 (C, CO).

IR (KBr) in $cm^{-1}$: 3054 (m), 3028 (m), 2912 (w), 1704 (s, broad) [$v_{c=o}$], 1596 (s, broad), 1454 (s), 1400 (w), 1317 (w), 1272 (s, broad), 1235 (m), 1192 (m), 750 (s, broad), 968 (s).

Example 3
Production of 1,3-dimethylindene

For this, the 3-methylindan-1-one produced in Example 1 (21.0 g, 0.144 mole) was dissolved in 20 ml of diethyl ether and added dropwise to a solution of methylmagnesium iodide in diethyl ether (the Grignard solution is prepared by adding methyl iodide (25.4 g, 11.3 ml, 0.18 mole) dropwise to a suspension of magnesium powder (4.4 g, 0.18 mole) in 40 ml of diethyl ether). After boiling for 2 hours under reflux the reaction mixture is poured onto 100 ml of iced water. The mixture is acidified with 5 N hydrochloric acid until the precipitated magnesium salts have dissolved. The aqueous and organic phases are separated and the aqueous phase is extracted twice with in each case 50 ml of diethyl ether. The combined organic phases are washed with 30 ml of each of a saturated $NaHCO_3$ solution, water and then with saturated NaCl solution. The organic phase is next freed from all volatile constituents in a rotary evaporator (40° C., 1013 mbar) and the residue is taken up in 120 ml of benzene. After adding p-toluenesulfonic acid (400 mg, 2.3 mmole) the mixture is boiled for 2 hours under reflux in a water separator. The solution is washed with 20 ml of saturated $NaHCO_3$ solution, and the organic phase is separated and dried over $Na_2SO_4$. The organic phase is then freed from all volatile constituents in a rotary evaporator (40° C., 240 mbar) and the residue is distilled under an oil pump vacuum at 51° C.

Yield: 12.0 g (0.0833 mole, 58% of theory referred to 3-methylindan-1-one).

$^1$H-NMR in $CDCl_3$, 300.0 MHz, [δ]: 1.31 (d, 3 H, $^2J_{HH}$=9.0 Hz, $CH_3$), 2.16 (s, 3 H, $CH_3$), 3.43 (q, 1 H, $^2J_{HH}$=9.0 Hz, C$\underline{H}$—$CH_3$), 6.16 (s, 1 H, $CH_3$—C=C$\underline{H}$), 7.2–7.4 (m, 4 H, CH, $C_9H_5$).

$^{13}C\{^1H\}$-NMR in $CDCl_3$, 75.5 MHz, [δ]: 12.9 ($CH_3$), 16.2 ($CH_3$), 43.6 ($\underline{C}H$—$CH_3$), 118.8 (CH), 122.4 (CH), 124.6 (CH), 126.2 (CH), 136.0 ($CH_3C$=$\underline{C}H$), 138.0 ($C_{ipso}$, C—$CH_3$), 145.2 ($C_{ipso}$ $C_9H_5$), 149.7 ($C_{ipso}$ $C_9H_5$).

IR (KBr) in $cm^{-1}$: 3053 (s), 2963 (s, broad), 1615 (s), 1455 (s), 1374 (s), 1071 (s), 1018 (s), 972 (s).

Example 4
Production of 1,3-diphenylindene 3-phenylindan-1-one from Example 2 (21.0 g, 0.144 mole) is dissolved in 20 ml of diethyl ether and added dropwise to a solution of phenylmagnesium bromide in diethyl ether (the Grignard solution is prepared by adding phenyl bromide (11.9 g, 8.8 ml, 0.0758 mole) dissolved in 25 ml of diethyl ether dropwise to magnesium powder (2.02 g, 0.0758 mole) in 25 ml of diethyl ether). The mixture is now heated under reflux for 1.5 hours, stirred for a further 15 hours at 25° C., and then poured onto 100 ml of iced water. The mixture is acidified with 5 N hydrochloric acid until the magnesium salts that were formed have dissolved. The organic phase is separated and the aqueous phase is extracted twice with in each case 50 ml of diethyl ether. The combined organic phases are separated with 30 ml of each of a saturated NaHCO$_3$ solution, water and then with saturated NaCl solution. The organic phase is next freed from all volatile constituents in a rotary evaporator (40° C., 1013 mbar) and the residue is taken up in 120 ml of benzene. After adding p-toluenesulfonic acid (400 mg, 2.3 mmole) the reaction mixture is boiled for 3 hours under reflux in a water separator. The solution is washed with 20 ml of saturated NaHCO$_3$ solution, and the organic phase is separated by means of a separating funnel and dried over Na$_2$SO$_4$. The organic phase is then freed again from all volatile constituents in a rotary evaporator, the residue is purified by column chromatography using silica gel as the stationary phase and petroleum ether as mobile phase (column diameter: 3.0 cm, filling height: 20 cm). A colorless solid is obtained.

Yield: 16.8 g (0.064 mole, 85% of theory referred to 3-phenylindan-1-one).

M.p.: 71° C.

$^1$H-NMR in CDCl$_3$, 300.0 MHz, [δ]: 4.78 (s, 1 H, CH—C$_6$H$_5$), 6.72 (s, 1 H, =CH—CH), 7.2–7.8 (m, 14 H, CH).

$^{13}$C{$^1$H}-NMR in CDCl$_3$, 75.5 MHz, [δ]: 55.4 (CH—C$_6$H$_5$), 120.5 (CH), 124.3 (CH), 125.6 (CH), 126.6 (CH), 126.7 (CH), 126.8 (CH), 127.7 (CH), 127.8 (CH), 127.8 (CH), 127.9 (CH), 128.0 (CH), 128.6 (CH), 128.6 (CH), 128.8 (CH), 135.6 (C$_{ipso}$, C$_6$H$_5$), 139.5 (C$_{ipso}$, C$_6$H$_5$), 143.1 (C$_{ipso}$, C$_9$H$_5$), 144.6 (C$_{ipso}$, C$_9$H$_5$), 149.2 (C$_{ipso}$, =C—C$_6$H$_5$).

IR (KBr) in cm$^{-1}$: 3059 (s), 3024 (s), 1489 (s), 1445 (s), 1345 (m), 1181 (m), 1153 (m), 1071 (s).

Example 5
Production of 2-bromo-1,3-dimethylindene 1,3-dimethylindene from Example 3 (4.9 g, 0.0343 mole) is dissolved at 25° C. in 150 ml of diethyl ether. Bromine (5.5 g, 1.76 ml, 0.0345 mole) is added dropwise at 0° C. After stirring for 3 hours at 25° C. all volatile constituents are removed under an oil pump vacuum. A brown oil is obtained. Purification is carried out by column chromatography using silica gel as stationary phase and a mixture of hexane and methylene chloride (10:1) as mobile phase (column diameter: 3.0 cm, filling height: 20 cm). A pale yellow oil is obtained.

Yield: 7.4 g (0.033 mole, 97% of theory referred to 1.3-dimethylindene).

Analysis: Calculated for C$_{11}$H$_{11}$Br(223.11): C, 59.22; H, 4.97. Found: C, 59.18; H, 4.94.

$^1$H-NMR in CDCl$_3$, 300.0 MHz, [δ]: 1.36 (d, 3 H, $^2$J$_{HH}$=7.5 Hz, CH$_3$), 2.12 (s, 3 H, CH$_3$), 3.43 (q, 1 H, $^2$J$_{HH}$=7.5 Hz, CH—CH$_3$), 7.2–7.4 (m, 4 H, CH, C$_9$H$_5$).

$^{13}$C{$^1$H}-NMR in CDCl$_3$, 75.5 MHz, [δ]: 12.4 (CH$_3$), 16.7 (CH$_3$), 48.9 (CH—CH$_3$), 119.1 (CH), 122.8 (CH), 125.5 (CH), 127.2 (CH), 129.9 (C$_{ipso}$, C—Br), 137.0 (C$_{ipso}$, C—CH$_3$), 144.0 (C$_{ipso}$, C$_9$H$_5$), 147.8 (C$_{ipso}$, C$_9$H$_5$).

IR (NaCl) in cm$^{-1}$: 3068 (m), 3017 (m), 2970 (s), 2928 (s), 2868 (m), 1617 (s), 1459 (s), 1377 (m), 1281 (m), 995 (s).

Example 6
Production of 2-bromo-1,3-diphenylindene

The 1,3-diphenylindene formed in Example 4 (5.0 g, 0.0186 mole) is dissolved at 25° C. in 150 ml of diethyl ether. Bromine (2.98 g, 0.96 ml, 0.0186 mole) is added dropwise at 0° C. After stirring for 3 hours at 25° C., all volatile constituents are removed under an oil pump vacuum. A viscous, brown oil is obtained. Purification is carried out by column chromatography using silica gel as stationary phase and a mixture of hexane and methylene chloride (10:1) as mobile phase (column diameter: 3.0 cm, filling height: 20 cm). A colorless solid is obtained.

For the X-ray structure analysis, suitable single crystals were obtained by crystallization at 25° C. from petroleum ether.

Yield: 6.3 g (0.0182 mole, 98% of theory referred to 1.3-diphenylindene).

Analysis: Calculated for C$_{21}$H$_{15}$Br(347.25): C, 72.64; H, 4.35. Found: C, 72.78; H, 4.39.

Mp: 82° C.

$^1$H-NMR in CDCl$_3$, 300.0 MHz, [δ]: 4.76 (s, 1 H, CH—C$_6$H$_5$), 7.2–7.7 (m, 14 H, CH, C$_6$H$_5$ and C$_9$H$_5$).

$^{13}$C{$^1$H}-NMR in CDCl$_3$, 62.9 MHz, [δ]: 61.5 (CH—C$_6$H$_5$), 120.5 (CH), 124.5 (CH), 126.3 (CH), 127.6 (CH), 127.9 (CH), 128.7 (CH), 128.8 (CH), 129.0 (CH), 129.0 (CH), 1.29.1 (CH), 129.2 (CH), 129.3 (CH), 129.5 (CH), 129.52 (C$_{ipso}$, C—Br), 133.9 (C$_{ipso}$, C—C$_6$H$_5$), 138.5 (C$_{ipso}$, C$_6$H$_5$), 143.0 (C$_{ipso}$, C$_6$H$_5$), 143.6 (C$_{ipso}$, C$_9$H$_5$), 147.7 (C$_{ipso}$, C$_9$H$_5$).

IR (KBr) in cm$^{-1}$: 3066 (m), 3025 (m), 1592 (s, broad), 1489 (m), 1450 (s), 1291 (w, broad), 1274 (w, broad), 1071 (m), 1027 (m).

Example 7
Production of 2-(tert.-butylaminodimethylsilyl)-1,3-dimethylindene

For this, the 2-bromo-1,3-dimethylindene obtained in Example 5 (2.5 g, 0.0112 mole) was dissolved in 5 ml of tetrahydrofuran and added dropwise to a mixture of magnesium powder (0.5 g, 0.02 mole) and dichlorodimethylsilane (3.9 g, 3.6 ml, 0.03 mole) in 15 ml of tetrahydrofuran. The solution boils (note: if no spontaneous heating of the reaction solution is observed, this can be initiated by adding a few drops of 1,2-dibromomethane). The reaction mixture is stirred for 15 hours at 25° C., following which all volatile constituents are removed under an oil pump vacuum. 40 ml of petroleum ether are now added and the suspension obtained is filtered to remove the magnesium salt. All volatile constituents are removed from the filtrate obtained under an oil pump vacuum. The pale yellow oil that is obtained is dissolved in 30 ml of diethyl ether and cooled to 0° C. Tert.-butylamine (2.16 g, 3.1 ml, 0.0296 mole) dried over NaH is now added. The mixture is stirred for 15 hours at 25° C. and all volatile constituents are then removed under an oil pump vacuum. 40 ml of petroleum ether are now added and the precipitated ammonium salt is filtered. After removing the solvent under an oil pump vacuum, the pale yellow oil that is obtained is distilled in a bulb tube distillation apparatus at 170° C. under an oil pump vacuum. A colorless oil is obtained.

Yield: 1.0 g (3.66 mmole, 32% of theory referred to 2-bromo-1,3-dimethylindene).

Analysis: Calculated for C$_{17}$H$_{27}$NSi (273.49): C, 74.66; H, 9.95. Found: C, 74.21; H, 9.60.

$^1$H-NMR in CDCl$_3$, 250.0 MHz, [δ]: 0.25 (s, 3 H, SiCH$_3$), 0.28 (s, 3 H, SiCH$_3$), 1.08 (s, 9 H, C(CH$_3$)$_3$), 1.25 (d, 3 H, $^2$J$_{HH}$=10.0 Hz, CH$_3$), 2.21 (s, 3 H, CH$_3$), 3.45 (q, 1 H, $^2$J$_{HH}$=10.0 Hz, CH—CH$_3$), 7.1–7.3 (m, 4 H, CH).

$^{13}$C{$^1$H}-NMR in CDCl$_3$, 62.9 MHz, [δ]: 3.1 (SiCH$_3$), 3.7 (SiCH$_3$), 13.9 (CH$_3$), 18.1 (CH$_3$), 33.8 (C(CH$_3$)$_3$), 48.9 (CH—CH$_3$), 49.7 (C(CH$_3$)$_3$),118.9 (CH), 122.4 (CH), 125.2 (CH), 126.3 (CH), 146.3 (=C—CH$_3$),147.3 (C$_{ipso}$, C$_9$H$_5$), 147.8 (C$_{ipso}$, C$_9$H$_5$), 152.4 (C—Si).

IR (NaCl) in cm$^{-1}$: 3382 (s) [$v_{NH}$], 3064 (s), 2956 (s, broad), 2867 (s), 1593 (m), 1556 (s), 1372 (s), 1297 (w), 1251 (s), [$v_{SiC}$], 1226 (s), 1094 (s, broad), 1025 (s, broad), 842 (s, broad).

Example 8

Production of 2-(tert.-butylaminodimethylsilyl)-1,3-diphenylindene 2-bromo-1,3-diphenylindene (Example 6) (2.5 g, 0.0072 mole) is dissolved in 5 ml of tetrahydrofuran and added dropwise to a mixture of magnesium powder (0.35 g, 0.0144 mole) and dichlorodimethylsilane (2.8 g, 2.6 ml, 0.0216 mole) in 10 ml of tetrahydrofuran. The solution boils. The solution is stirred for 15 hours at 25° C., following which all volatile constituents are removed under an oil pump vacuum. 40 ml of petroleum ether are now added and the magnesium salt is separated by filtration through a G3 frit. All volatile constituents are removed from the filtrate obtained under an oil pump vacuum. The pale yellow oil that is obtained is dissolved in 30 ml of diethyl ether and cooled to 0° C. Tert.-butylamine (2.16 g, 3.1 ml, 0.0296 mole) dried over NaH is now added. The reaction mixture is stirred for 15 hours at 25° C., tert.-BuNH$_2$.HCl separating out. All volatile constituents are then removed under an oil pump vacuum. 40 ml of petroleum ether are next added to the residue and filtered from the precipitated tert.-BuNH$_2$.HCl through a G4 frit. After removing the solvent under an oil pump vacuum, the pale yellow oil that is obtained is distilled at 254° C. in a bulb tube distillation apparatus under an oil pump vacuum. A viscous, colorless oil is obtained.

Yield: 1.36 g (3.4 mmole, 48% of theory referred to 2-bromo-1,3-diphenylindene).

Analysis: Calculated for C$_{27}$H$_{31}$NSi (397.63): C, 81.56; H, 7.86. Found: C, 81.13; H, 7.64.

$^1$H-NMR in CDCl$_3$, 250.0 MHz, [δ]: −0.11 (s, 3 H, SiCH$_3$), 0.00 (s, 3 H, SiCH$_3$),0.97 (s, 9 H, C(CH$_3$), 4.88 (s, 1 H, C$\underline{H}$—C$_6$H$_5$), 7.1–7.3 (m, 10 H, CH), 7.4–7.8 (m, 4 H, CH).

$^{13}$C{$^1$H}-NMR in CDCl$_3$, 62.9 MHz, [δ]: 3.2 (SiCH$_3$), 4.0 (SiCH$_3$), 33.6 (C($\underline{C}$H$_3$)$_3$), 49.5 ($\underline{C}$(CH$_3$)$_3$), 60.9 ($\underline{C}$H—C$_6$H$_5$), 120.6 (CH), 123.9 (CH), 125.6 (CH), 126.0 (CH), 126.8 (CH), 126.8 (CH), 127.5 (CH), 127.8 (CH), 128.0 (CH), 128.2 (CH), 128.4 (CH), 128.5 (CH), 128.7 (CH), 129.6 (CH), 137.9 (C$_{ipso}$, C$_6$H$_5$), 140.7 (C$_{ipso}$, C$_6$H$_5$), 146.2 (C$_{ipso}$, C$_9$H$_4$), 149.5 (C$_{ipso}$, C$_9$H$_4$), 152.1 (C$_{ipso}$, $\underline{C}$—C$_6$H$_5$), 154.5 (C—Si).

IR (NaCl) in cm$^{-1}$: 3382 (s) [$v_{NH}$], 3064 (s), 2956 (s, broad), 2867 (s), 1593 (m), 1556 (s), 1372 (s), 1297 (w), 1251 (s), [$v_{SiC}$], 1226 (s), 1094 (s, broad), 1025 (s, broad), 842 (s, broad).

Example 9

Production of 2-(cyclopentadienyldimethylsilyl)-1,3-dimethylindene

The 2-bromo-1,3-dimethylindene obtained in Example 5 (2.5 g, 0.0112 mole) is dissolved in 5 ml of tetrahydrofuran and added dropwise to a mixture consisting of magnesium powder (0.5 g, 0.02 mole) and dichlorodimethylsilane (3.9 g, 3.6 ml, 0.03 mole) in 15 ml of tetrahydrofuran. The solution boils. The reaction solution is stirred for 15 hours at 25° C., following which all volatile constituents are removed under an oil pump vacuum. 40 ml of petroleum ether are now added and the magnesium salt is separated by filtration through a G3 frit. All volatile constituents are removed from the filtrate obtained under an oil pump vacuum. The pale yellow oil that is obtained is dissolved in 30 ml of diethyl ether and cooled to 0° C. Cyclopentadienylsodium (1.0 g, 0.0112 mole) dissolved in 10 ml of tetrahydrofuran is now added. The reaction mixture is stirred for 15 hours at 25° C., following which all volatile constituents are removed under an oil pump vacuum. 35 ml of petroleum ether are next added and filtered from the precipitated NaCl through diatomaceous earth (G4 frit). The residue is purified by column chromatography using silica gel as stationary phase and a mixture of hexane and methylene chloride (10:1) as mobile phase (column diameter: 3.0 cm, filling height: 20 cm). A pale yellow oil is obtained.

Yield: 0.856 g (3.2 mmole, 29% of theory referred to 2-bromo-1,3-dimethylindene).

Analysis: Calculated for C$_{18}$H$_{22}$Si (266.46): C, 81.12; H, 8.34. Found: C, 81.25; H, 8.17.

$^1$H-NMR in CDCl$_3$, 250.0 MHz, [δ]: 0.00 (s, 3 H, SiCH$_3$), 0.15 (s, 3 H, SiCH$_3$), 1.25 (d, 3 H, $^3$J$_{HH}$=10.0 Hz, CH$_3$), 2.28 (s, 3 H, CH$_3$), 3.40 (q, 1 H, $^3$J$_{HH}$=10.0 Hz, C$\underline{H}$—CH$_3$), 3.52 (s, 1 H, C$\underline{H}$—Si(CH$_3$)$_2$), 6.5–6.7 (m, 4 H, C$_5$H$_5$), 6.9–7.1 (m, 4 H, C$_9$H$_4$).

$^{13}$C{$^1$H}-NMR in CDCl$_3$, 62.9 MHz, [δ]: −3.1 (SiCH$_3$), −2.0 (SiCH$_3$), 13.0 (CH$_3$), 15.4 (CH$_3$), 48.0 ($\underline{C}$H—CH$_3$), 50.0 (CH—Si), 119.0 (CH), 122.4 (CH), 125.3 (CH), 126.6 (CH), 130.8 (=CH, C$_5$H$_5$),133.1 (=CH, C$_5$H$_5$), 144.2 (C$_{ipso}$), 145.9 (C$_{ipso}$) 148.9 (C$_{ipso}$, $\underline{C}$—CH$_3$), 152.2 (C$_{ipso}$, C—Si).

IR (NaCl) in cm$^{-1}$: 3066 (s), 3016 (s), 2960 (s), 2868 (s), 1939 (w), 1899 (w), 1792 (w), 1590 (m), 1557 (s), 1464 (s), 1338 (s), 1250 (s) [$v_{SiC}$], 1118 (s), 973 (s), 950 (s), 907 (s).

Example 10

Production of 2-(cyclopentadienyldimethylsilyl)-1,3-diphenylindene 2-bromo-1,3-diphenylindene (2.5 g, 0.0072 mole) from Example 6 is dissolved in 5 ml of tetrahydrofuran and added dropwise to a mixture consisting of magnesium powder (0.35 g, 0.0144 mole) and dichlorodimethylsilane (2.8 g, 2.6 ml, 0.0216 mole) in 10 ml of tetrahydrofuran. The solution boils. The reaction solution is stirred for 15 hours at 25° C., following which all volatile constituents are removed under an oil pump vacuum. 40 ml of petroleum ether are added and the suspension obtained is filtered through a G4 frit to remove the magnesium salt. All volatile constituents are removed from the filtrate obtained under an oil pump vacuum. The pale yellow oil that is obtained is dissolved in 20 ml of diethyl ether and cooled to 0° C. Cyclopentadienylsodium (0.634 g, 0.0072 mole) dissolved in 5 ml of tetrahydrofuran is now added. The reaction mixture is stirred for 15 hours at 25° C., following which all volatile constituents are removed under an oil pump vacuum. 35 ml of petroleum ether are next added and filtered from the precipitated sodium chloride. The residue is purified by column chromatography using silica gel as stationary phase and a mixture of hexane and methylene chloride (10:1) as mobile phase (column diameter: 3.0 cm, filling height: 20 cm). A pale yellow, viscous oil is obtained.

Yield: 0.98 g (2.5 mole, 35% of theory referred to 2-bromo-1,3-dimethylindene).

Analysis: Calculated for C$_{28}$H$_{26}$Si (390.60): C, 86.06; H, 6.72. Found: C, 85.98; H, 6.75.

$^1$H-NMR in CDCl$_3$, 250.0 MHz, [δ]: −0.25 (s, 3 H, SiCH$_3$), 0.00 (s, 3 H, SiCH$_3$), 3.35 (s, 1 H, CH—Si), 5.05 (s, 1 H, C$\underline{H}$—C$_6$H$_5$), 6.5–6.7 (m, 4 H, C$_5$H$_5$), 7.2–7.7 (m, 4 H, C$_9$H$_4$).

$^{13}$C{$^1$H}-NMR in CDCl$_3$, 62.9 MHz, [δ]: −3.9 (SiCH$_3$), −1.6 (SiCH$_3$), 42.5 ($\underline{C}$H—Si), 61.1 ($\underline{C}$H—C$_6$H$_5$), 120.6 (CH), 123.9 (CH), 125.6 (CH), 126.0 (CH), 126.8 (CH), 126.8 (CH), 127.5 (CH), 127.8 (CH), 128.0 (CH), 128.2

(CH), 128.4 (CH), 128.5 (CH), 128.7 (CH), 129.6 (CH), 130.8 (=CH, C$_5$H$_5$),133.1 (=CH, C$_5$H$_5$), 137.9 (C$_{ipso}$, C$_6$H$_5$), 140.7 (C$_{ipso}$, C$_6$H$_5$), 146.2 (C$_{ipso}$, C$_9$H$_5$), 149.5 (C$_{ipso}$, C$_9$H$_5$), 152.1 (C$_{ipso}$, C—C$_6$H$_5$), 154.5 (C—Si).

IR (NaCl) in cm$^{-1}$: 3027 (s), 2961 (s), 2879 (s), 1951 (m), 1882 (m), 1809 (m), 1759 (m), 1599 (s), 1499 (s), 1455 (s), 1336 (s), 1288 (s) 1274 (s), 1257 (s) [v$_{SiC}$], 1192 (s), 1159 (s), 1087 (s), 1029 (s), 1001 (s), 919 (s), 884 (s), 774 (s).

Example 11

Production of 2-(tert.-butylaminodimethylsilyl)-1,3-dimethylindene titanium dichloride The 2-(tert.-butylaminodimethylsilyl)-1,3-dimethylindene produced in Example 7 (0.68 g, 2.48 mmole) is dissolved in 10 ml of petroleum ether and metallized at −78° C. with a 2.5 N solution of n-BuLi in hexane (2.1 ml, 4.96 mmole). A yellow solid precipitates at −50° C. The reaction mixture is heated to 25° C. within 3 hours in a cooling bath. The supernatant liquid is pipetted from the precipitated dilithium salt and the residue is dried under an oil pump vacuum.

TiCl$_3$.3THF (0.918 g, 2.48 mmole) is suspended in 5 ml of tetrahydrofuran and cooled to −78° C. The dilithium salt is dissolved in 10 ml of tetrahydrofuran and cooled to −78° C. This solution is transferred to the TiCl$_3$.3THF suspension using a cannula. The reaction mixture is heated within 3 hours to 25° C. The color of the reaction mixture changes from yellow to red. AgCl (0.720 g, 4.96 mmole) is now added in a single portion. The reaction mixture is stirred for 45 minutes at 25° C., following which all volatile constituents are removed under an oil pump vacuum. The residue is taken up in 30 ml of toluene and the reaction mixture is filtered through diatomaceous earth (G4 frit). After removing the toluene under an oil pump vacuum 20 ml of petroleum ether are added, a reddish-brown solid precipitating out. The supernatant liquid is decanted from the solid. The residue is dried under an oil pump vacuum. A reddish-brown powder is obtained.

Yield: 0.55 g (1.41 mmole, 57% of theory referred to 2-(tert.-butylaminodimethylsilyl)-1,3-dimethylindene).

Analysis: Calculated for C$_{17}$H$_{25}$Cl$_2$NSiTi (390.27): C, 52.32; H, 6.46. Found: C, 52.00; H, 6.26.

M.p.: 146° C.

$^1$H-NMR in CDCl$_3$, 250.0 MHz, [δ]: 0.80 (s, 6 H, SiCH$_3$), 1.30 (s, 9 H, C(CH$_3$), 2.45 (s, 6 H, CH$_3$), 7.35 (dd, 2 H, $^2J_{HH}$=7.4 H, $^3J_{HH}$=3.5 H, C$_9$H$_4$), 7.60 (dd, 2 H, $^2J_{HH}$=7.4 H, $^3J_{HH}$=3.5 H, C$_9$H$_4$).

$^{13}$C{$^1$H}-NMR in CDCl$_3$, 62.9 MHz, [δ]: 5.8 (Si(CH$_3$)$_2$), 16.4 (CH$_3$), 33.7 (C(CH$_3$)$_3$), 64.3 (C(CH$_3$)$_3$), 123.1 (CH), 124.8 (C—Si), 127.9 (CH), 134.2 (C$_{ipso}$, C$_9$H$_4$), 135.1 (C$_{ipso}$, C$_9$H$_4$).

IR (CaF$_2$, dissolved in CDCl$_3$) in cm$^{-1}$: 3057 (m), 2970 (s), 2929 (s), 2874 (s), 1589 (s, broad), 1499 (m), 1462 (m), 1448 (m), 1403 (m), 1380 (m), 1364 (m), 1293 (w) 1256 (s) [v$_{SiC}$], 1216 (m), 1182 (s), 1102 (s), 1028 (m, broad), 981 (s), 930 (s).

Example 12

Production of 2-(tert.-butylaminodimethylsilyl)-1,3-diphenylindene zirconium dichloride For this, the 2-(tert.-butylaminodimethylsilyl)-1,3-diphenylindene produced in Example 8 (0.705 g, 1.77 mmole) was dissolved in 10 ml of petroleum ether and metallized at −78° C. with a 2.5 M solution of n-BuLi in hexane (1.5 ml, 3.55 mmole). A yellow solid precipitates at −50° C. The reaction mixture is heated to 25° C. within 3 hours in a cooling bath. The supernatant liquid is pipetted off from the precipitated dilithium salt and is washed twice with in each case 10 ml of petroleum ether. The residue is then dried under an oil pump vacuum.

The dilithium salt Li$_2${2-(1,3-Ph$_2$C$_9$H$_5$)SiMe$_2$NH tert.-Bu} is dissolved in 8 ml of toluene and cooled to −78° C. Zirconium tetrachloride (0.412 g, 1.77 mmole) is suspended in 8 ml of toluene and added to the solution of the dilithium salt formed above. The reaction mixture is heated within 3 hours to 25° C., the color of the reaction mixture changing from pale yellow to yellowish-orange. The reaction mixture is stirred for 15 hours at 25° C. and filtered through diatomaceous earth (G4 frit). After removing the toluene under an oil pump vacuum, 15 ml of petroleum ether are added, whereupon a yellow solid precipitates out. The supernatant liquid is decanted from the solid and the residue is dried under an oil pump vacuum. A yellow powder is obtained.

Yield: 0.6 g (1.07 mmole, 61% of theory referred to 2-(tert.-butylaminodimethyl-silyl)-1,3-diphenylindene).

M.p.: 125° C.

$^1$H-NMR in CDCl$_3$, [δ]: 0.00 (s, 6 H, SiMe$_2$), 1.27 (s, 9 H, CMe$_3$), 7.28 (dd, 2 H, $^2J_{HH}$=7.6 Hz, $^3J_{HH}$=3.4 Hz, C$_9$H$_4$), 7.4–7.5 (m, 10 H, C$_6$H$_5$), 7.66 (dd, 2 H, $^2J_{HH}$=7.6 Hz, $^3J_{HH}$=3.4 Hz, C$_9$H$_4$).

$^{13}$C{$^1$H}-NMR in CDCl$_3$, [δ]: 5.3 (SiMe$_2$), 33.4 (C(CH$_3$)$_3$), 58.8 (C(CH$_3$)$_3$), 122.5 (CH, C$_9$H$_4$), 127.4 (CH, C$_9$H$_4$), 128.5 (CH, C$_6$H$_5$), 128.5 (CH, C$_6$H$_5$), 129.7 (CH, C$_6$H$_5$) 134.0 (CSi, C$_9$H$_4$), 132.4 (C$_{ipso}$, C$_6$H$_5$), 134.8 (C$_{ipso}$, C$_9$H$_4$), 134.9 (C$_{ipso}$, C$_9$H$_4$).

IR (CaF$_2$, dissolved in CDCl$_3$) in cm$^{-1}$: 3061 (m, broad), 2958 (s, broad), 2929 (s), 2870 (s), 1954 (w), 1900 (w), 1811 (w), 1598 (s, broad), 1497 (m), 1460 (m), 1450 (m), 1402 (m) 1384 (m) 1364 (m), 1293 (w), 1256 (s) [v$_{SiC}$], 1185 (s), 1099 (m), 1077 (s), 1029 (s), 991 (s).

Example 13

Production of 2-(cyclopentadienyldimethylsilyl)-1,3-dimethylindene zirconocene dichloride 2-(cyclopentadienedimethylsilyl)-1,3-dimethylindene (0.53 g, 1.99 mmole) from Example 9 is dissolved in 10 ml of diethyl ether and metallized at −78° C. with a 2.5 N solution of n-BuLi in hexane (1.6 ml, 3.98 mole). After heating to 25° C., the reaction mixture is stirred for a further 4 hours. All volatile constituents are then removed under an oil pump vacuum, the residue is washed twice with in each case 15 ml of petroleum ether, and the dilithium salt is suspended in 15 ml of toluene. The suspension is now cooled to −20° C. Zirconium tetrachloride (0.465 g, 2.00 mmole) suspended in 10 ml of toluene is added and the mixture is stirred for 15 hours at 25° C. All volatile constituents are now removed under an oil pump vacuum, the residue is washed with 5 ml of petroleum ether and the petroleum ether is removed under an oil pump vacuum. 30 ml of methylene chloride are now added and the solution is filtered through a G4 frit using diatomaceous earth to remove all insoluble constituents. A lemon-yellow solid is obtained after removing the methylene chloride under an oil pump vacuum.

Yield: 0.44 g (1.03 mmole, 52% of theory referred to 2-(cyclopentadienyldimethyl-silyl)-1,3-dimethylindene).

Analysis: Calculated for C$_{18}$H$_{20}$Cl$_2$SiZr (426.56): C, 50.68; H, 4.74. Found: C, 51.04; H, 4.75.

M.p.: from 155° C. (continuous decomposition without melting).

$^1$H-NMR in CDCl$_3$, 250.0 MHz, [δ]: 0.90 (s, 6 H, Si(CH$_3$)$_2$), 2.30 (s, 6 H, CH$_3$),5.85 (pt, 2 H, J$_{HH}$=2.4 H, C$_5$H$_4$), 6.80 (pt, 2 H, J$_{HH}$=2.4 H, C$_5$H$_4$), 7.25 (dd, 2 H,$^2$J$_{HH}$=7.5 H, $^3$J$_{HH}$=3.7 H, C$_9$H$_4$), 7.48 (dd, 2 H $^2$J$_{HH}$=7.5 H, $^3$J$_{HH}$=3.7 H, C$_9$H$_4$).

$^{13}$C{$^1$H}-NMR in CDCl$_3$, 62.9 MHz, [δ]: −0.5 (Si(CH$_3$)$_2$), 14.7 (CH$_3$), 113.9 (CH, Cp), 117.0 (C—Si, C$_5$H$_4$), 124.0

(CH, $C_5H_4$), 126.2 (CH, $C_9H_4$), 128.2 (CH, $C_9H_4$), 137.5 ($C_{ipso}$, $C_9H_4$), 140.0 ($C_{ipso}$, C—$CH_3$), 145.0 (C—Si, $C_9H_4$).

IR (KBr) in $cm^{-1}$: 3178 (s, broad), 3066 (s), 2962 (s), 1951 (w), 1918 (w), 1895 (w), 1867 (w), 1774 (w), 1746 (w), 1648 (m, broad), 1459 (w), 1394 (m) 1365 (m) 1259 (m) [$v_{SiC}$], 1166 (m), 1051 (m), 838 (s), 816 (s), 774 (s).

Example 14

Production of 2-(cyclopentadienyldimethylsilyl)-1,3-diphenylindene zirconocene dichloride The 2-(cyclopentadienedimethylsilyl)-1,3-diphenylindene produced in Example 10 (0.81 g, 2.077 mmole) is dissolved in 25 ml of diethyl ether and metallized at –78° C. with a 2.5 N solution of n-BuLi in hexane (1.7 ml, 4.15 mole). The reaction mixture is heated to 25° C. and stirred for a further 4 hours. All volatile constituents are then removed under an oil pump vacuum, and the residue is washed twice with in each case 15 ml of petroleum ether and suspended in 20 ml of toluene. The suspension is now cooled to –20° C. Zirconium tetrachloride (0.48 g, 2.06 mmole) suspended in 15 ml of toluene is added and the mixture is stirred for 15 hours at 25° C. All volatile constituents are removed under an oil pump vacuum, and the residue is washed with 10 ml of petroleum ether and then dried under an oil pump vacuum. 30 ml of methylene chloride are now added and the solution is filtered through diatomaceous earth (G4 frit) to remove all insoluble constituents. A canary-yellow solid is obtained after removing the methylene chloride under an oil pump vacuum. Suitable single crystals for the X-ray structure analysis (FIG. 1) were obtained by crystallization at –20° C. from methylene chloride.

Yield: 1.033 g (1.87 mmole, 90% of theory referred to 2-(cyclopentadienyldimethyl-silyl)-1,3-diphenylindene).

Analysis: Calculated for $C_{28}H_{24}Cl_2SiZr$ (550.71): C, 61.06; H, 4.40. Found: C, 60.86; H, 4.10.

M.p.: 129° C.

$^1$H-NMR in $CDCl_3$, 250.0 MHz, [δ]: 0.00 (s, 6 H, Si($CH_3$)$_2$), 5.62 (pt, 2 H, $J_{HH}$=2.4 H, $C_5H_4$), 6.85 (pt, 2 H, $J_{HH}$=2.4 H, $C_5H_4$), 7.0–7.2 (m, 6 H, $C_6H_5$), 7.25 (dd, 2 H, $^2J_{HH}$=7.5 H, $^3J_{HH}$=3.7H, $C_9H_4$), 7.2–7.3(m, 6 H, $C_6H_5$), 7.45 (dd, 2 H, $^2J_{HH}$=7.5 H, $^3J_{HH}$=3.7 H, $C_9H_4$), $^{13}C\{^1H\}$-NMR in $CDCl_3$, 62.9 MHz, [δ]: 0.0 (Si($CH_3$)$_2$), 113.0 (C—Si, $C_5H_4$), 115.2 (CH, $C_5H_4$), 124.4 (CH, $C_5H_4$), 127.2 (CH, $C_9H_4$), 128.8 (CH, $C_9H_4$), 128.9 (CH, $C_6H_5$), 129.4 (CH, $C_6H_5$), 129.7 (CH, $C_6H_5$), 132.0 ($C_{ipso}$ C—$C6H_5$), 133.8 ($C_{ipso}$ $C_6H_5$), 135.6 ($C_{ipso}$ $C_9H_5$), 140.0 (C—Si, $C_9H_5$).

IR (KBr) in $cm^{31\ 1}$: 3397 (s, broad), 1945 (w), 1906 (w), 1864 (w), 1822 (w), 1745 (w), 1628 (m, broad), 1599 (w), 1498 (w), 1445 (w), 1385 (w), 1254 (m) [$v_{SiC}$], 1178 (m), 1073 (m), 1047 (m), 1001 (m), 846 (s), 820 (s), 798 (s), 758 (s).

Example 15

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 2.0 mg (5 μmoles) of 2-(tert.-butylaminodimethylsilyl)-1,3-dimethylindene titanium dichloride from Example 11 in 2.5 ml of toluene was then added. The internal temperature was adjusted to 30° C. with a thermostat. 15 g of ethylene and 14.4 g of propylene were then metered in. The polymerization was started by adding a solution of 37 mg (40 μmoles) of triphenylmethyl-tetrakis-(pentafluorophenyl) borate in 8 ml of toluene. 5 ml of ENB were then added through a pressure lock. Ethylene and propylene were continuously metered in a weight ratio of 50:50 so that the pressure remained constant at 6 bar at 30° C. After 25 minutes' polymerization the autoclave pressure was released. For the working-up the polymer was precipitated in methanol and dried for 20 hours at 60° C. in vacuo, 41.1 g of copolymer being obtained. The IR spectroscopic determination of the composition of the copolymer showed an incorporation of 47.3 wt. % of ethylene, 46.8 wt. % of propylene and 6.3 wt. % of ENB. A rubber-like polymer was obtained that has a Mooney value of 28.2.

Example 16

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 2.0 mg (5 μmoles) of 2-(tert.-butylaminodimethylsilyl)-1,3-dimethylindene titanium dichloride from Example 11 in 2.5 ml of toluene was then added. The internal temperature was adjusted to 60° C. with a thermostat. 11 g of ethylene and 10 g of propylene were then metered in. The polymerization was started by adding a solution of 4.6 mg (5 μmoles) of triphenylmethyltetrakis(pentafluorophenyl) borate in 1 ml of toluene. 5 ml of ENB were then added through a pressure lock. Ethylene and propylene were continuously metered in a weight ratio of 50:50 so that the pressure remained constant at 6 bar at 60° C. After 20 minutes' polymerization a solution of 46 mg (50 μmoles) of triphenylmethyl-tetrakis (pentafluorophenyl) borate in 10 ml of toluene was metered again into the autoclave. After a total polymerization time of 50 minutes the autoclave pressure was released. For the working-up the polymer was precipitated in methanol and dried for 20 hours at 60° C. in vacuo, 37.1 g of copolymer being obtained. The IR spectroscopic determination of the composition of the copolymer showed an incorporation of 47.6 wt. % of ethylene, 44.6 wt. % of propylene and 8.5 wt. % of ENB. A rubber-like polymer was obtained that has a Mooney value of 105.2.

Example 17 (Comparison Example with (2-indSiMe$_2$Ntert.-Bu)TiCl$_2$)

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 5.4 mg (15 μmoles) of 2-(tert.-butylaminodimethylsilyl)-indene titanium dichloride in 7.5 ml of toluene was then added. The internal temperature was adjusted to 30° C. with a thermostat. 17.2 g of ethylene and 15.3 g of propylene were then metered in. The polymerization was started by adding a solution of 55.3 mg (60 μmoles) of triphenylmethyl-tetrakis (pentafluorophenyl) borate in 12 ml of toluene. 5 ml of ENB were then added through a pressure lock. Ethylene and propylene were continuously metered in a weight ratio of 50:50 so that the pressure remained constant at 6 bar at 30° C. After 40 minutes' polymerization the autoclave pressure was released. For the working-up the polymer was precipitated in methanol and dried for 20 hours at 60° C. in vacuo, 43.8 g of copolymer being obtained. A rubber-like polymer was obtained that has a Mooney value of 22.6.

Example 18 (Comparison Example with Me₄CpSiMe₂Ntert.-Bu)TiCl₂)

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 5.4 mg (15 μmoles) of 2-(tert.-butylaminodimethylsilyl)-tetramethylcyclopentadiene titanium dichloride in 7.5 ml of toluene was then added. The internal temperature was adjusted to 30° C. with a thermostat. 17.2 g of ethylene and 15.3 g of propylene were then metered in. The polymerization was started by adding a solution of 55.3 mg (60 μmoles) of triphenylmethyl-tetrakis(pentafluoro-phenyl) borate in 12 ml of toluene. 5 ml of ENB were then added through a pressure lock. Ethylene and propylene were continuously metered in a weight ratio of 50:50 so that the pressure remained constant at 6 bar at 30° C. After 40 minutes' polymerization the autoclave pressure was released. For the working-up the polymer was precipitated in methanol and dried for 20 hours at 60° C. in vacuo, 43.8 g of copolymer being obtained. A rubber-like polymer was obtained that has a Mooney value of 22.6.

Example 19 (Comparison Example with (2-etrahydroindacenyl)SiMe₂Ntert.-Bu)TiCl₂)

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 2.0 mg (10 μmoles) of 2-(tert.-butylaminodimethylsilyl)-tetrahydroindacene titanium dichloride in 2.5 ml of toluene was then added. The internal temperature was adjusted to 60° C. with a thermostat. 13.3 g of ethylene and 12.9 g of propylene were then metered in. The polymerization was started by adding a solution of 37 mg (40 μmoles) of triphenylmethyl-tetrakis (pentafluorophenyl) borate in 20 ml of toluene. 5 ml of ENB were then added through a pressure lock. Ethylene and propylene were continuously metered in a weight ratio of 50:50 so that the pressure remained constant at 6 bar at 60° C. After 60 minutes' polymerization the autoclave pressure was released. For the working-up the polymer was precipitated in methanol and dried for 20 hours at 60° C. in vacuo, 21 g of copolymer being obtained.

Example 20 (Comparison Example with Me₄CpSiMe₂Ntert.-Bu)TiCl₂)

Terpolymerization of Ethylene, Propylene and 5-ethylidene-2-norbonene (ENB)

500 ml of hexane and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 1.8 mg (5 μmoles) of 2-(tert.-butylaminodimethylsilyl)-tetramethylcyclopentadiene titanium dichloride in 2.5 ml of toluene was then added. The internal temperature was adjusted to 60° C. with a thermostat. 9.9 g of ethylene and 8.9 g of propylene were then metered in. The polymerization was started by adding a solution of 25.3 mg (27.5 μmoles) of triphenylmethyl-tetrakis-(pentafluorophenyl) borate in 11 ml of toluene. 5 ml of ENB were then added through a pressure lock. Ethylene and propylene were continuously metered in a weight ratio of 50:50 so that the pressure remained constant at 6 bar at 60° C. After 40 minutes' polymerization the autoclave pressure was released. For the working-up the polymer was precipitated in methanol and dried for 20 hours at 60° C. in vacuo, 36.9 g of copolymer being obtained. A rubber-like polymer was obtained that has a Mooney value of 24.7.

Example 21

Copolymerization of Ethylene and Propylene 500 ml of toluene and 1 ml of TIBA were placed in a 1.4 l capacity steel autoclave equipped with a mechanical stirrer, manometer, temperature sensor, a temperature control device, a catalyst lock and monomer metering devices for ethylene and propylene. A solution of 1.4 mg (2.5 μmoles) of 2-(cyclopentadienyldimethylsilyl)-1,3-diphenylindene zirconocene dichloride from Example 14 in 1.25 ml of toluene was then added. The internal temperature was adjusted to 40° C. with a thermostat. 30.5 g of propylene (2.8 bar) and 13.5 g of ethylene (total pressure up to 7 bar) were then metered in. The polymerization was started by adding a solution of 4.6 mg (5 μmoles) of triphenylmethyl-tetrakis (pentafluorophenyl) borate in 2.5 ml of toluene. During the polymerization, the internal temperature rose to 53° C. After 12 minutes' polymerization the autoclave pressure was released. For the working-up the polymer was precipitated in methanol and dried for 20 hours at 60° C. in vacuo, 32.9 g of copolymer being obtained. A rubber-like polymer was obtained. The IR spectroscopic determination of the composition of the copolymer showed an incorporation of 72.0 wt. % of ethylene and 28.0 wt. % of propylene. A glass transition temperature of −46° C. was measured by the DSC method. The measurement of the intrinsic viscosity gave a value of 1.8 dl/g.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of organometallic compounds of transition metals with 2-indenyl as ligand disubstituted in the 1,3-position, that correspond to the general formula (I),

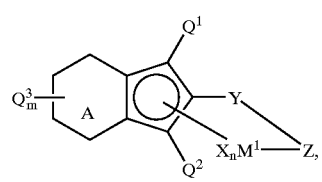

(I)

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphos-phoryl, $Q^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge selected from the group consisting of —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— or —$Si(R^1R^2)$—$Si(R^3R^4)$—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —$N(R^5)$—, —$P(R^6)$—, |$N(R^5R^7)$—, |$P(R^6R^8)$—, —O—, —S—, |$OR^5$— or |$SR^5$—, wherein the vertical lines to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may, in addition denote —$Si(R^1R^2R^3)$, and $R^6$ and $R^8$ may in addition denote —$Si(R^1R^2R^3)$, —$OR^1$, —$SR^1$— or —$N(R^1R^2)$, comprising the step of reacting a halogenated indene substituted in the 1,3-position of the formula

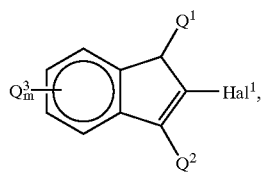

(II)

in which $Hal^1$ denotes Cl, Br or I and $Q^1$, $Q^2$ and $Q^3$ have the above meanings, with an elementary metal selected from Groups I, II or XII of the Periodic System according to IUPAC 1985 or a corresponding metal compound in an amount in the range from 1 to 100 moles of elementary metal/metal compound per mole of (II) and with a dihalide of the bridge Y of the formula $Hal^2$—Y—$Hal^3$, (III), in which $Hal^2$ and $Hal^3$ independently of one another denote Cl, Br or I and Y has the above range of meanings, in an amount of 1 to 20 moles of (III) per mole of (II), wherein if Y has the meaning —$Si(R^1R^2)$—, —$Ge(R^1R^2)$— or —$Si(R^1R^2)$—$Si(R^3R^4)$—, the reaction of (II) with (i) elementary metal/metal compound, and of (ii) with (III) may also take place simultaneously, and the reaction product of the formula

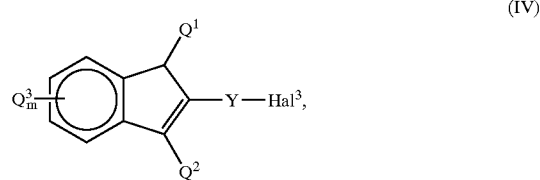

(IV)

wherein $Q^1$, $Q^2$, $Q^3$, Y, $Hal^3$ and m have the above meanings, is reacted, optionally after it has been separated, with a Z derivative of the formula $ZM^2_p$ (Va)

or $ZR^9_p$ (Vb), in which $M^2$ denotes Li, Na, K or —$MgHal^4$, wherein $Hal^4$ has the range of meanings of $Hal^2$, p represents the number 1 or 2, $R^9$ denotes hydrogen, —$Si(R^1R^2R^3)$ or —$Sn(R^1R^2R^3)$, and Z, $R^1$, $R^2$ and $R^3$ have the above meanings, with the release of a compound of the formula $M^2Hal^3$ (VIa)

or $R^9Hal^3$ (VIb), in which $M^2$, $R^9$ and $Hal^3$ have the above meanings, optionally in the presence of an auxiliary base to form the 2-indenyl compound of the formula

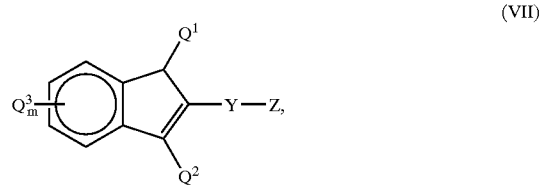

(VII)

in which $Q^1$, $Q^2$, $Q^3$, Y, Z and m have the above meanings and which may be present as a dianion, and in which Z may, furthermore, carry $M^2$, $R^9$ or an electron pair, and is then reacted further with a transition metal compound of the formula $M^1X_q$ (VIII), in which $M^1$ and X have the above meanings and q is a number from 2 to 6 that is determined by the oxidation state of $M^1$.

2. A process according to claim 1, wherein Y is a bridge selected from the group consisting of —$Si(R^1R^2)$—, —$Ge(R^1R^2)$— and $Si(R^1R^2)$—$Si(R^3R^4)$—, and the reaction of (II) with (i) an elementary metal/metal compound and (ii) with (III) to form the reaction product takes place simultaneously.

3. A process according to claim 2, wherein Y is —Si(R$^1$R$^2$)—.

4. A process according to claim 1, wherein Mg or Zn or a mixture of Mg and Zn is used as elementary metal.

5. A process according to claim 1, wherein M$^1$ is a transition metal selected from the group consisting of Ti, Zr, Hf, V, or Nb.

6. A process according to claim 5, wherein M$^1$ is a transition metal selected from the group consisting of Ti, Zr, or Hf.

7. A process according to claim 6, wherein M$^1$ is a transition metal selected from the group consisting of Ti or Zr.

8. A process according to claim 1, wherein from 1 to 10 moles of elementary metal/metal compound are used per mole of (II) and 1 to 10 moles of (III) are used per mole of (II).

9. Organometallic compounds of transition metals with 2-indenyl as ligand substituted in the 1,3-position, that correspond to the general formula (I)

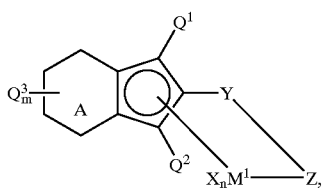

(I)

wherein

A denotes the benzo system or the tetrahydrocyclohexyl system,

Q$^1$, Q$^2$ are identical or different and, as substituent of the 2-indenyl system substituted in the 1,3-position, denote hydrogen, C$_1$–C$_4$-alkyl, C$_6$–C$_{14}$-aryl, C$_7$–C$_{10}$-aralkyl, C$_1$–C$_4$-alkoxy, C$_1$–C$_4$-alkylthio, phenoxy, phenylthio, di-C$_1$–C$_4$-alkylamino, C$_6$–C$_{14}$-aryl-C$_1$–C$_4$-alkylamino, di-C$_6$–C$_{14}$-arylamino, dibenzylamino, tri-C$_1$–C$_4$-alkylsilyl, di-C$_1$–C$_4$-alkylboranyl, phenyl-C$_1$–C$_4$-alkylboranyl, diphenylboranyl, di-C$_1$–C$_4$-alkylphosphoryl, diphenylphosphoryl or phenyl-C$_1$–C$_4$-alkylphosphoryl, Q$^3$ are identical or different and, as substituent of the 2-indenyl system substituted in the 4,5,6,7-position, denote hydrogen, C$_1$–C$_4$-alkyl, C$_6$–C$_{14}$-aryl, C$_7$–C$_{10}$-aralkyl, C$_1$–C$_4$-alkoxy, C$_1$–C$_4$-alkylthio, phenoxy, phenylthio, di-C$_1$–C$_4$-alkylamino, C$_6$–C$_{14}$-aryl-C$_1$–C$_4$-alkylamino, di-C$_6$–C$_{14}$-arylamino, dibenzylamino, tri-C$_1$–C$_4$-alkylsilyl, di-C$_1$–C$_4$-alkylboranyl, phenyl-C$_1$–C$_4$-alkylboranyl, diphenylboranyl, di-C$_1$–C$_4$-alkylphosphoryl, diphenylphosphoryl or phenyl-C$_1$–C$_4$-alkylphosphoryl, M$^1$ is a transition metal from Group IV, V or VI of the Periodic System of the Elements according to IUPAC 1985, X denotes an anion, n is a number from zero to 4 that is determined by the valency and the bonding state of M$^1$, m is a number from zero to 4 that is determined by the number of the radicals Q$^3$, Y is a bridge selected from the group consisting of —C(R$^1$R$^2$)—, —Si(R$^1$R$^2$)—, —Ge(R$^1$R$^2$)—, —C(R$^1$R$^2$)—C(R$^3$R$^4$)—, —C(R$^1$R$^2$)—Si(R$^3$R$^4$)— or —Si(R$^1$R$^2$)—Si(R$^3$R$^4$)—, wherein R$^1$, R$^2$, R$^3$ and R$^4$ independently of one another denote hydrogen, halogen, straight-chain or branched C$_1$–C$_{10}$-alkyl, C$_5$–C$_8$-cycloalkyl, C$_6$–C$_{14}$-aryl or C$_7$–C$_{10}$-aralkyl, and Z is a second ligand from the group of open-chain and cyclic, optionally anionic π-systems, —N(R$^5$)—, —P(R$^6$)—, |N(R$^5$R$^7$)—, |P(R$^6$R$^8$)—, —O—, —S—, |OR$^5$— or |SR$^5$—, wherein the vertical lines to the left of the element symbol N, P, O and S denotes an electron pair, and the bonding between Z and M$^1$ is ionic, covalent or co-ordinative, and wherein R$^5$, R$^6$, R$^7$ and R$^8$ independently of one another have the same range of meanings as R$^1$ to R$^4$, and R$^5$ and R$^7$ may in addition denote —Si(R$^1$R$^2$R$^3$), and R$^6$ and R$^8$ may in addition denote —Si(R$^1$R$^2$R$^3$), —OR$^1$, —SR$^1$ or —N(R$^1$R$^2$).

10. Organometallic compounds of transition metals according to claim 9, wherein in formula (I), Z is replaced by the second ligand Z', which denotes substituted or unsubstituted cyclopentadienyl, substituted or unsubstituted 1-indenyl, substituted or unsubstituted 2-indenyl, substituted or unsubstituted fluorenyl, —N(R$^5$)—, —P(R$^6$)—, |N(R$^5$R$^7$)—, |P(R$^6$R$^8$)—, —O—, —S—, |OR$^5$— or |SR$^5$—.

11. Organometallic compounds of transition metals according to claim 10, wherein in formula (I), Z' is replaced by the second ligand Z'', which denotes —N(R$^5$)— or |N(R$^5$R$^7$)—, wherein in formula (I) Y furthermore denotes —Si(R$^1$R$^2$)— and M$^1$ denotes Ti or Zr.

12. An organometallic compound of transition metals according to claim 9, wherein said organometallic compound is 2-(tert.-butylaminodimethylsilyl)-1,3-diphenylindene zirconium dichloride or 2-(tert.-butylaminodimethylsilyl)-1,3-dimethylindene titanium dichloride.

13. Intermediate products of the formula

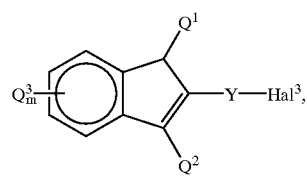

(IV)

in which

Q$^1$, Q$^2$ are identical or different and, as substituent of the 2-indenyl system substituted in the 1,3-position, denote hydrogen, C$_1$–C$_4$-alkyl, C$_6$–C$_{14}$-aryl, C$_7$–C$_{10}$-aralkyl, C$_1$–C$_4$-alkoxy, C$_1$–C$_4$-alkylthio, phenoxy, phenylthio, di-C$_1$–C$_4$-alkylamino, C$_6$–C$_{14}$-aryl-C$_1$–C$_4$-alkylamino, di-C$_6$–C$_{14}$-arylamino, dibenzylamino, tri-C$_1$–C$_4$-alkylsilyl, di-C$_1$–C$_4$-alkylboranyl, phenyl-C$_1$–C$_4$-alkylboranyl, diphenylboranyl, di-C$_1$–C$_4$-alkylphosphoryl, diphenyiphosphoryl or phenyl-C$_1$–C$_4$-alkylphosphoryl, Q$^3$ are identical or different and, as substituent of the 2-indenyl system substituted in the 4,5,6,7-position, denote hydrogen, C$_1$–C$_4$-alkyl, C$_6$–C$_{14}$-aryl, C$_7$–C$_{10}$-aralkyl, C$_1$–C$_4$-alkoxy, C$_1$–C$_4$-alkylthio, phenoxy, phenylthio, di-C$_1$–C$_4$-alkylamino, C$_6$–C$_{14}$-aryl-C$_1$–C$_4$-alkylamino, di-C$_6$–C$_{14}$-arylamino, dibenzylamino, tri-C$_1$–C$_4$-alkylsilyl, di-C$_1$–C$_4$-alkylboranyl, phenyl-C$_1$–C$_4$-alkylboranyl, diphenylboranyl, di-C$_1$–C$_4$-alkylphosphoryl, diphenylphosphoryl or phenyl-C$_1$–C$_4$-alkylphosphoryl, m is a number from zero to 4 that is determined by the number of the radicals Q$^3$, Y is a bridge from the group consisting of —C(R$^1$R$^2$)—, —Si(R$^1$R$^2$)—, —Ge(R$^1$R$^2$)—, —C(R$^1$R$^2$)—C $(R^3R^4)$—, —$C(R^1R^2)$—$Si(R^3R^4)$— or —$Si(R^1R^2)$—Si$(R^3R^4)$—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and $Hal^3$ denotes Cl, Br or I.

14. A process for the production of Intermediate products of the formula

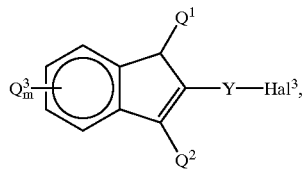

(IV)

in which

Q$^1$, Q$^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphos-phoryl, Q$^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, m is a number from zero to 4 that is determined by the number of the radicals Q$^3$, Y is a bridge selected from the group consisting of —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— or —$Si(R^1R^2)$—$Si(R^3R^4)$—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and $Hal^3$ denotes Cl, Br or I, comprising the step of reacting a 2-halogenated indene disubstituted in the 1,3-position of the formula

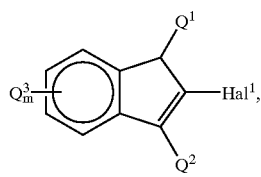

(II)

in which $Hal^1$ denotes Cl, Br or I, with an elementary metal selected from Groups I, II or XII of the Periodic System of the Elements according to IUPAC 1985 or a corresponding metal compound in an amount in the range from 1 to 100 moles of metal/metal compound per mole of (II) and with a dihalide of Y of the formula $Hal^2$—Y—$Hal^3$ (III), in which $Hal^2$ and $Hal^3$ independently of one another denote Cl, Br or I, in an amount of 1 to 20 moles of (III) per mole of (II), wherein in the case where Y denotes —$Si(R^1R^2)$—, —$Ge(R^1R^2)$— or —$Si(R^1R^2)$—$Si(R^3R^4)$—, the reaction of (II) with (i) elementary metal/metal compound and of (ii) with (III) may also take place simultaneously.

15. Catalysts for the polymerization of monomers selected from the group consisting of $C_2$–$C_{12}$-α-olefins, $C_4$–$C_{20}$-diolefins and cyclo(di)olefins or for the copolymerization of said monomers, said catalysts comprising organometallic compounds of transition metals with 2-indenyl as ligand substituted in the 1,3-position, that correspond to the general formula (I)

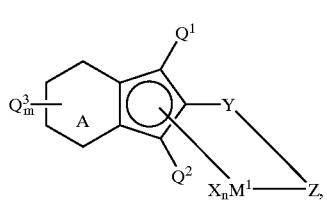

(I)

wherein

A denotes the benzo system or the tetrahydrocyclohexyl system,

Q$^1$, Q$^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, Q$^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, M$^1$ is a transition metal from Group IV, V or VI of the Periodic System of the Elements according to IUPAC 1985, X denotes an anion, n is a number from zero to 4 that is determined by the valency and the bonding state of M$^1$, m is a number from zero to 4 that is determined by the number of the radicals Q$^3$, Y is a bridge selected from the group consisting of —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— or —Si($R^1R^2$)—Si($R^3R^4$)—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—, |O$R^5$— or |S$R^5$—, wherein the vertical lines to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —O$R^1$, —S$R^1$ or —N($R^1R^2$).

16. The production of amorphous, substantially atactic polymers comprising organometallic compounds of transition metals with 2-indenyl as ligand substituted in the 1,3-position, that correspond to the general formula (I)

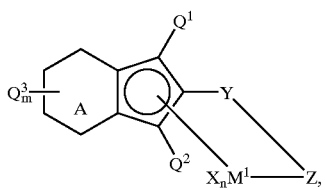

(I)

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge selected from the group consisting of —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—Si($R^3R^4$)—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—, |O$R^5$— or |S$R^5$—, wherein the vertical lines to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —O$R^1$, —S$R^1$ or —N($R^1R^2$).

17. The production of EP(D)M comprising organometallic compounds of transition metals with 2-indenyl as ligand substituted in the 1,3-position, that correspond to the general formula (I)

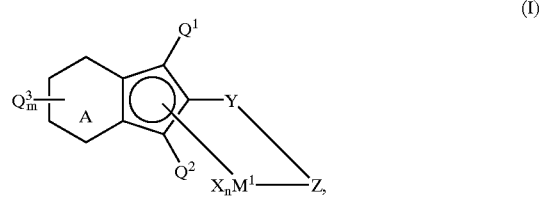

(I)

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ are identical or different and, as substituent of the 2-indenyl system substituted in the 4,5,6,7-position, denote hydrogen, $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge selected from the group consisting of —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—Si($R^3R^4$)—, wherein $R^1$, $R^2$, $R^3$ and $R^4$ independently of one another denote hydrogen, halogen, straight-chain or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—,

|OR⁵— or |SR⁵—, wherein the vertical lines to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —OR¹, —SR¹ or —N($R^1R^2$).

18. The production of atactic polypropylene comprising organometallic compounds of transition metals with 2-indenyl as ligand substituted in the 1,3-position, that correspond to the general formula (I)

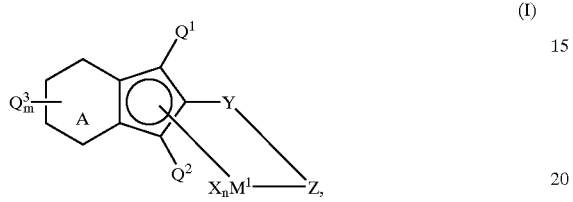

(I)

wherein

A denotes the benzo system or the tetrahydrocyclohexyl system, $Q^1$, $Q^2$ are identical or different and, as substituent of the 2-indenyl system substituted in the 1,3-position, denote hydrogen, $C_1-C_4$-alkyl, $C_6-C_{14}$-aryl, $C_7-C_{10}$-aralkyl, $C_1-C_4$-alkoxy, $C_1-C_4$-alkylthio, phenoxy, phenylthio, di-$C_1-C_4$-alkylamino, $C_6-C_{14}$-aryl-$C_1-C_4$-alkylamino, di-$C_6-C_{14}$-arylamino, dibenzylamino, tri-$C_1-C_4$-alkylsilyl, di-$C_1-C_4$-alkylboranyl, phenyl-$C_1-C_4$-alkylboranyl, diphenylboranyl, di-$C_1-C_4$-alkylphosphoryl, diphenylphosphoryl or phenyl-$C_1-C_4$-alkylphosphoryl, $Q^3$ are identical or different and, as substituent of the 2-indenyl system substituted in the 4,5,6,7-position, denote hydrogen, $C_1-C_4$-alkyl, $C_6-C_{14}$-aryl, $C_7-C_{10}$-aralkyl, $C_1-C_4$-alkoxy, $C_1-C_4$-alkylthio, phenoxy, phenylthio, di-$C_1-C_4$-alkylamino, $C_6-C_{14}$-aryl-$C_1-C_4$-alkylamino, di-$C_6-C_{14}$-arylamino, dibenzylamino, tri-$C_1-C_4$-alkylsilyl, di-$C_1-C_4$-alkylboranyl, phenyl-$C_1-C_4$-alkylboranyl, diphenylboranyl, di-$C_1-C_4$-alkylphosphoryl, diphenylphosphoryl or phenyl-$C_1-C_4$-alkylphosphoryl, $M^1$ is a transition metal from Group IV, V or VI of the Periodic System of the Elements according to IUPAC 1985, X denotes an anion, n is a number from zero to 4 that is determined by the valency and the bonding state of $M^1$, m is a number from zero to 4 that is determined by the number of the radicals $Q^3$, Y is a bridge selected from the group consisting of —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—Si($R^3R^4$)—, wherein $R^1$, $R^2$, $R^3$ and $R^4$ independently of one another denote hydrogen, halogen, straight-chain or branched $C_1-C_{10}$-alkyl, $C_5-C_8$-cycloalkyl, $C_6-C_{14}$-aryl or $C_7-C_{10}$-aralkyl, and Z is a second ligand from the group of open-chain and cyclic, optionally anionic π-systems, —N($R^5$)—, —P($R^6$)—, |N($R^5R^7$)—, |P($R^6R^8$)—, —O—, —S—, |OR⁵— or |SR⁵—, wherein the vertical lines to the left of the element symbol N, P, O and S denotes an electron pair, and the bonding between Z and $M^1$ is ionic, covalent or co-ordinative, and wherein $R^5$, $R^6$, $R^7$ and $R^8$ independently of one another have the same range of meanings as $R^1$ to $R^4$, and $R^5$ and $R^7$ may in addition denote —Si($R^1R^2R^3$), and $R^6$ and $R^8$ may in addition denote —Si($R^1R^2R^3$), —OR¹, —SR¹ or —N($R^1R^2$).

* * * * *